(12) United States Patent
Sham et al.

(10) Patent No.: US 9,968,797 B2
(45) Date of Patent: *May 15, 2018

(54) ELECTROMAGNETIC THERMAL THERAPY

(75) Inventors: Kin-Joe Sham, Shoreview, MN (US); Jared J. Savela, Maplewood, MN (US); Kristopher M. Siverhus, Victoria, MN (US); John F. Dinusson, Saint Louis Park, MN (US)

(73) Assignee: OrthoCor Medical, Inc., Arden Hills, MN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/541,509

(22) Filed: Jul. 3, 2012

(65) Prior Publication Data

US 2012/0330090 A1 Dec. 27, 2012

Related U.S. Application Data

(63) Continuation-in-part of application No. 12/831,779, filed on Jul. 7, 2010, now Pat. No. 8,768,454, which
(Continued)

(51) Int. Cl.
*A61F 7/00* (2006.01)
*A61N 2/00* (2006.01)
(Continued)

(52) U.S. Cl.
CPC ............... *A61N 2/02* (2013.01); *A61F 7/007* (2013.01); *A61N 2/002* (2013.01); *A61F 7/034* (2013.01);
(Continued)

(58) Field of Classification Search
CPC ...... A61F 2007/0042; A61F 7/03; A61F 7/00; A61F 7/106; A61F 2007/0078;
(Continued)

(56) References Cited

U.S. PATENT DOCUMENTS 4,173,218 A 11/1979 Cronin
4,240,445 A 12/1980 Iskander et al.
(Continued)

FOREIGN PATENT DOCUMENTS

CN 1072347 A 5/1993
WO WO-2004069128 A1 8/2004
(Continued)

OTHER PUBLICATIONS

"U.S. Appl. No. 12/104,007 Notice of Allowance dated Jun. 30, 2010", 9 pgs.
(Continued)

*Primary Examiner* — Michael Carey
*Assistant Examiner* — Pamela M Bays
(74) *Attorney, Agent, or Firm* — Schwegman Lundberg & Woessner, P.A.

(57) ABSTRACT

A portable, non-invasive device for providing therapeutic treatment to a joint to promote healing of the joint includes a cuff positionable around the joint. The cuff includes an electromagnetic stimulator configured to provide an electromagnetic field within the joint and at least one thermal therapy component including an activation circuit configured to activate the electromagnetic stimulator circuit, the thermal therapy component coupleable to the cuff, the thermal therapy component comprising at least two substances in separate compartments separated by a breakable barrier, wherein the at least two substances are configured to react upon mixing to produce thermal energy exchangeable with the joint.

17 Claims, 25 Drawing Sheets

Related U.S. Application Data is a continuation-in-part of application No. 12/104,007, filed on Apr. 16, 2008, now Pat. No. 7,783,348.

(60) Provisional application No. 60/983,653, filed on Oct. 30, 2007, provisional application No. 60/927,354, filed on May 3, 2007.

(51) Int. Cl.
*A61N 2/02* (2006.01)
*A61F 7/03* (2006.01)
*A61N 1/32* (2006.01)

(52) U.S. Cl.
CPC .............. *A61F 2007/0042* (2013.01); *A61F 2007/0078* (2013.01); *A61F 2007/0096* (2013.01); *A61N 1/32* (2013.01); *A61N 2/006* (2013.01)

(58) Field of Classification Search
CPC ........ A61F 2007/023; A61F 2007/0276; A61F 7/007; A61N 2/02; A61N 1/35021; A61N 2/002; A61N 2/004; A61N 2/006; A61N 2/06
USPC .............. 600/14, 15; 607/2, 3, 50, 51, 108
See application file for complete search history.

(56) References Cited

U.S. PATENT DOCUMENTS

| | | | |
|---|---|---|---|
| 4,256,116 A | 3/1981 | Meretsky et al. |
| 4,412,540 A | 11/1983 | Bentall |
| 4,548,208 A | 10/1985 | Niemi |
| 4,674,482 A | 6/1987 | Waltonen et al. |
| 4,727,857 A | 3/1988 | Horl |
| 4,757,804 A | 7/1988 | Griffith et al. |
| 4,886,063 A | 12/1989 | Crews |
| 4,981,135 A | 1/1991 | Hardy |
| 4,989,604 A | 2/1991 | Fang |
| 5,000,178 A | 3/1991 | Griffith |
| 5,014,699 A | 5/1991 | Pollack et al. |
| 5,179,942 A | 1/1993 | Drulias et al. |
| 5,181,902 A | 1/1993 | Erickson et al. |
| 5,314,401 A | 5/1994 | Tepper |
| 5,336,255 A | 8/1994 | Kanare et al. |
| 5,401,233 A | 3/1995 | Erickson et al. |
| 5,411,542 A | 5/1995 | Jensen |
| 5,478,303 A | 12/1995 | Foley-Nolan et al. |
| 5,487,759 A | 1/1996 | Bastyr et al. |
| 5,578,065 A | 11/1996 | Hattori et al. |
| 5,584,863 A | 12/1996 | Rauch et al. |
| 5,718,721 A | 2/1998 | Ross |
| 5,723,001 A | 3/1998 | Pilla et al. |
| 5,743,844 A | 4/1998 | Tepper et al. |
| 5,792,213 A | 8/1998 | Bowen |
| 5,860,945 A | 1/1999 | Cramer et al. |
| 5,904,710 A | 5/1999 | Davis et al. |
| 5,922,012 A | 7/1999 | Sakano |
| 5,947,913 A | 9/1999 | Palumbo |
| 5,951,459 A | 9/1999 | Blackwell |
| 6,024,691 A | 2/2000 | Tepper et al. |
| 6,042,531 A | 3/2000 | Holcomb |
| 6,096,067 A | 8/2000 | Cramer et al. |
| 6,129,659 A | 10/2000 | Wilk |
| 6,132,362 A | 10/2000 | Tepper et al. |
| 6,186,941 B1 | 2/2001 | Blackwell |
| 6,200,259 B1 | 3/2001 | March |
| 6,213,934 B1 | 4/2001 | Kaufman et al. |
| 6,228,108 B1 | 5/2001 | Lamb et al. |
| 6,261,221 B1 | 7/2001 | Tepper et al. |
| 6,275,737 B1 | 8/2001 | Mann |
| 6,334,069 B1 | 12/2001 | George et al. |
| 6,353,763 B1 | 3/2002 | George et al. |
| 6,436,020 B1 | 8/2002 | Weingand |
| 6,443,883 B1 | 9/2002 | Ostrow et al. |
| 6,445,955 B1 * | 9/2002 | Michelson et al. ............ 607/46 |
| 6,463,336 B1 | 10/2002 | Mawhinney |
| 6,465,709 B1 | 10/2002 | Sun et al. |
| 6,506,403 B1 | 1/2003 | Yu |
| 6,551,233 B2 | 4/2003 | Perreault et al. |
| 6,561,968 B1 | 5/2003 | Dissing et al. |
| 6,589,159 B2 | 7/2003 | Paturu |
| 6,592,509 B1 | 7/2003 | Hunter, Jr. |
| 6,602,213 B1 | 8/2003 | Figley |
| 6,606,519 B2 | 8/2003 | Powell |
| 6,641,520 B2 | 11/2003 | Bailey et al. |
| 6,652,446 B1 | 11/2003 | Bove et al. |
| 6,675,047 B1 | 1/2004 | Konoplev et al. |
| 6,678,562 B1 | 1/2004 | Tepper et al. |
| 6,701,185 B2 | 3/2004 | Burnett et al. |
| 6,839,595 B2 | 1/2005 | Tepper et al. |
| 6,875,188 B2 | 4/2005 | Chiang |
| 6,955,642 B1 | 10/2005 | Simon |
| 7,008,369 B2 | 3/2006 | Cuppen |
| 7,022,506 B2 | 4/2006 | Brighton et al. |
| 7,087,076 B2 | 8/2006 | Purcell |
| 7,130,692 B2 | 10/2006 | Brighton et al. |
| 7,175,587 B2 | 2/2007 | Gordon et al. |
| 7,215,995 B2 | 5/2007 | Brighton et al. |
| 7,336,993 B1 | 2/2008 | Szeles |
| 7,551,957 B2 | 6/2009 | Whelan et al. |
| 7,740,574 B2 | 6/2010 | Pilla et al. |
| 7,744,524 B2 | 6/2010 | Pilla |
| 7,758,490 B2 | 7/2010 | Pilla et al. |
| 7,783,348 B2 | 8/2010 | Gill et al. |
| 8,768,454 B2 | 7/2014 | Sham et al. |
| 2001/0018605 A1 | 8/2001 | Helming |
| 2002/0143373 A1 | 10/2002 | Courtnage et al. |
| 2004/0010178 A1 | 1/2004 | Buckner |
| 2004/0044384 A1 * | 3/2004 | Leber et al. .................... 607/88 |
| 2004/0097855 A1 | 5/2004 | Page et al. |
| 2004/0097856 A1 * | 5/2004 | Cipra et al. ...................... 602/7 |
| 2004/0176803 A1 | 9/2004 | Whelan et al. |
| 2004/0176805 A1 | 9/2004 | Whelan et al. |
| 2004/0176806 A1 | 9/2004 | Markoll |
| 2005/0049653 A1 | 3/2005 | Wang |
| 2005/0087194 A1 | 4/2005 | Scott |
| 2005/0182287 A1 | 8/2005 | Becker |
| 2006/0041292 A1 | 2/2006 | Bowen |
| 2006/0190043 A1 | 8/2006 | Brighton et al. |
| 2007/0106354 A1 | 5/2007 | Carstens |
| 2007/0167990 A1 | 7/2007 | Mangrum et al. |
| 2007/0255187 A1 | 11/2007 | Branch |
| 2008/0039810 A1 | 2/2008 | Lee et al. |
| 2008/0132971 A1 | 6/2008 | Pille et al. |
| 2008/0185946 A1 | 8/2008 | Meckert et al. |
| 2008/0288035 A1 | 11/2008 | Gill et al. |
| 2010/0222631 A1 | 9/2010 | Pilla |
| 2011/0004261 A1 | 1/2011 | Sham et al. |
| 2011/0065977 A1 | 3/2011 | Sham et al. |
| 2014/0046232 A1 | 2/2014 | Sham et al. |

FOREIGN PATENT DOCUMENTS

| | | |
|---|---|---|
| WO | WO-2006096698 A2 | 9/2006 |
| WO | WO-2006115119 A1 | 11/2006 |
| WO | WO-2008137319 A1 | 11/2008 |
| WO | WO-2012005766 A1 | 1/2012 |

OTHER PUBLICATIONS

"U.S. Appl. No. 12/104,007, Examiner Interview Summary dated Jul. 8, 2010", 1 pg.

"U.S. Appl. No. 12/104,007, Non Final Office Action dated Oct. 21, 2009", 28 pgs.

"U.S. Appl. No. 12/104,007, Response filed Mar. 22, 2010 to Non Final Office Action dated Oct. 21, 2009", 18 pgs.

"U.S. Appl. No. 12/831,779 , Response filed Jun. 19, 2013 to Non Final Office Action dated Dec. 19, 2012", 11 pgs.

"U.S. Appl. No. 12/831,779, Final Office Action dated Nov. 22, 2013", 17 pgs.

"U.S. Appl. No. 12/831,779, Non Final Office Action dated Dec. 19, 2012", 13 pgs.

(56) References Cited

OTHER PUBLICATIONS

"U.S. Appl. No. 12/831,779, Notice of Allowance dated Feb. 14, 2014", 9 pgs.

"U.S. Appl. No. 12/831,779, Preliminary Amendment dated Jul. 16, 2010", 3 pgs.

"U.S. Appl. No. 12/831,779, Response filed Jan. 22, 2014 to Final Office Action dated Nov. 22, 2013", 9 pgs.

"U.S. Appl. No. 12/882,878, Final Office Action dated Sep. 10, 2014", 11 pgs.

"U.S. Appl. No. 12/882,878, Non Final Office Action dated Feb. 25, 2014", 17 pgs.

"U.S. Appl. No. 12/882,878, Response filed Aug. 25, 2014 to Non Final Office Action dated May 25, 2014", 10 pgs.

"U.S. Appl. No. 14/054,683, Non Final Office Action dated Oct. 9, 2014", 14 pgs.

"U.S. Appl. No. 14/054,683, Response filed Aug. 25, 2014 to Restriction Requirement dated Jun. 25, 2014", 7 pgs.

"U.S. Appl. No. 14/054,683, Restriction Requirement dated Jun. 25, 2014", 6 pgs.

"CDRH Document Imaging System: Folder K903675", (Nov. 1992), 77 pgs.

"Chinese Application Serial No. 201180038759.3, Office Action dated May 28, 2014", w/English Translation, 15 pgs.

"European Application Serial No. 11735708.7, Examination Notification Art. 94(3) dated Sep. 25, 2014", 4 pgs.

"International Application Serial No. PCT/US2008/061214, International Preliminary Report on Patentability dated Nov. 3, 2009", 7 pgs.

"International Application Serial No. PCT/US2008/061214, International Search Report and Written Opinion dated Jul. 8, 2008", 14 pgs.

"International Application Serial No. PCT/US2011/001187, International Preliminary Report on Patentability dated Jan. 17, 2013", 8 pgs.

"International Application Serial No. PCT/US2011/001187, Search Report dated Sep. 23, 114", 4 pgs.

"International Application Serial No. PCT/US2011/001187, Written Report dated Sep. 23, 2011", 7 pgs.

"Ivivi SofPulse: Premarket Notification [501(k)] Summary", Ivivi Technologies Inc., (Dec. 2008), 5 pgs.

"OrthoCor Active Knee System: Premarket Notification [501(k)] Summary", Orthocor Medical, Inc., (Dec. 2009), 5 pgs.

Fini, et al., "Effects of pulsed electromagnetic fields on articular hyaline cartilage: review of experimental and clinical studies", Biomedicine & Pharmacotherapy 59, (Feb. 2005), 388-394.

Pilla, A. A, et al., "EMF signals and ion/ligand binding kinetics: prediction of bioeffective waveform parameters", Bioelectrochemistry and Bioenergetics, 48(1), (Feb. 1999), 27-34.

Sutbeyaz, et al., "The effect of pulsed electromagnetic of fields in the treatment of cervical osteoarthritis: a randomized, double-blink, sham-controlled trial", Rheumatol Int, 26, (Jan. 2006), 320-324.

"U.S. Appl. No. 15/207,258, Final Office Action dated Jun. 14, 2017", 11 pgs.

"U.S. Appl. No. 12/882,878, Non Final Office Action dated Aug. 11, 2015", 15 pgs.

"U.S. Appl. No. 12/882,878, Response filed Mar. 10, 2015 to Final Office Action dated Sep. 10, 2014", 13 pgs.

"Chinese Application Serial No. 201180038759.3, Office Action dated Mar. 25, 2015", 13 pgs.

"Chinese Application Serial No. 201180038759.3, Response filed Dec. 11, 2014 to Non Final Office Action dated Jun. 11, 2014", W/ English Claims, (dated Dec. 11, 2014), 8 pgs.

"European Application Serial No. 11735708.7 Response filed Mar. 17, 2015 to Examination Notification Art. 94(3) dated Sep. 25, 2014", With the amended claims, 15 pgs.

\* cited by examiner

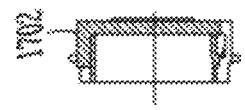
FIG. 17F
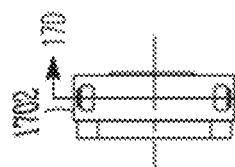
FIG. 17E
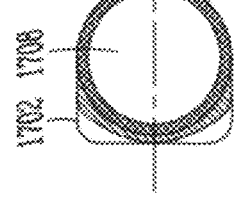
FIG. 17D
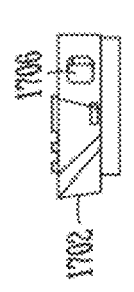  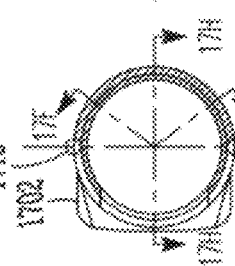 
FIG. 17I  FIG. 17H  FIG. 17C  FIG. 17G
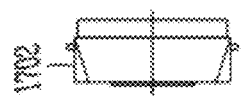
FIG. 17B
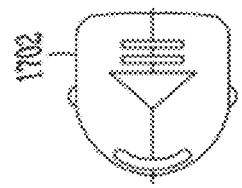
FIG. 17A

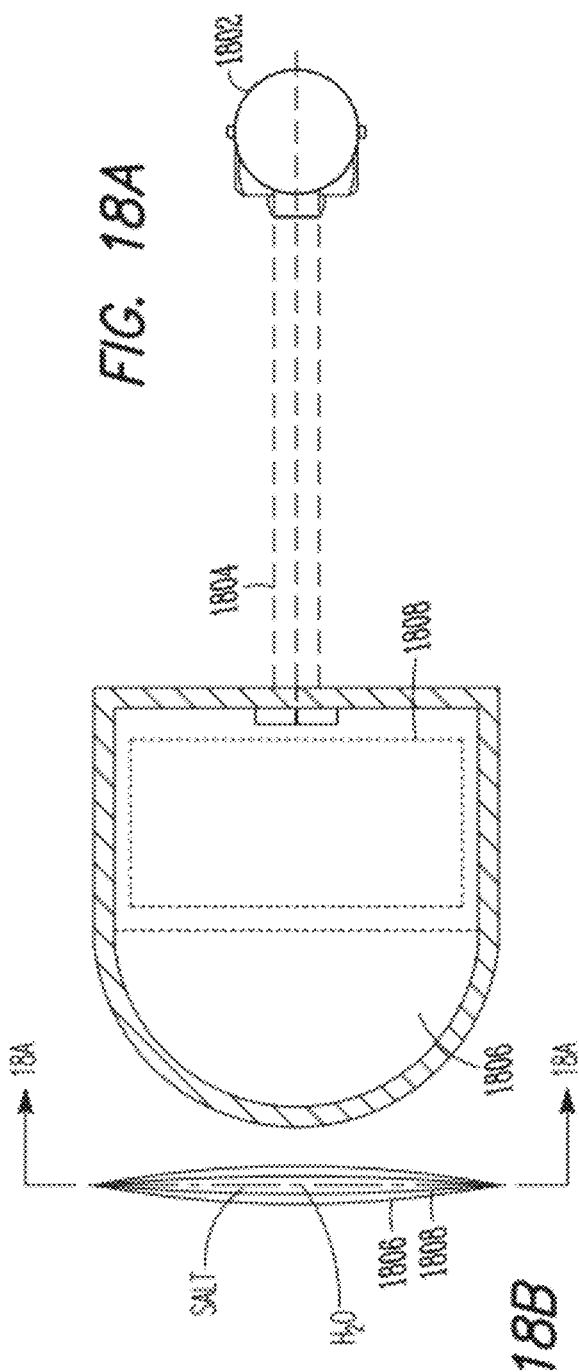

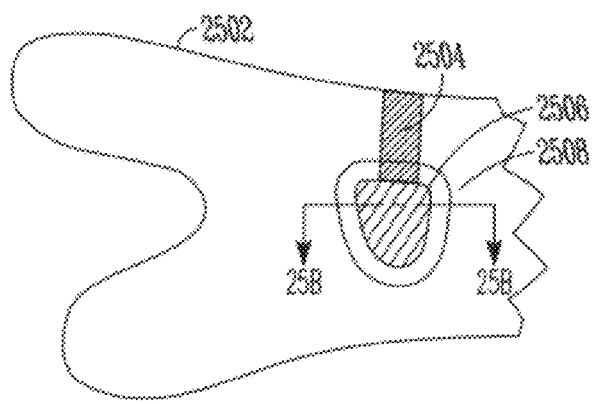
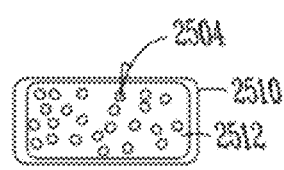
FIG. 25A  FIG. 25B
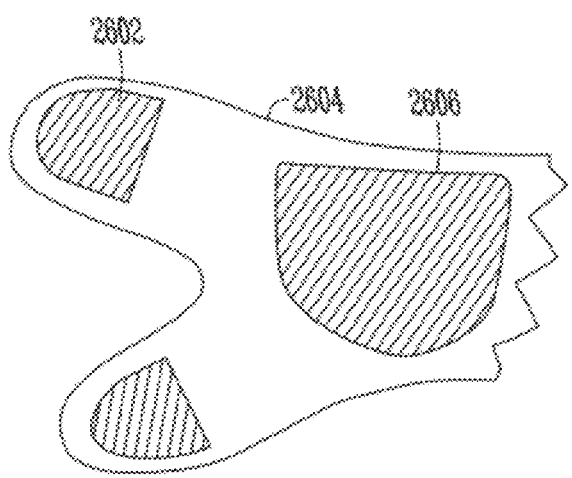
FIG. 26

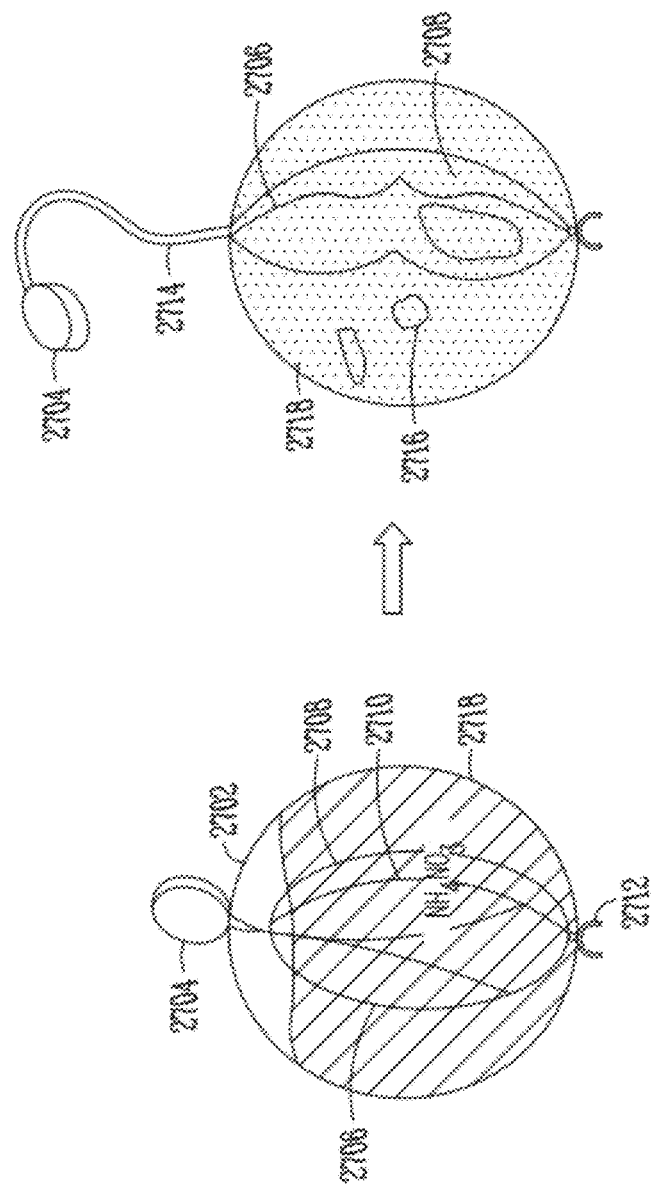

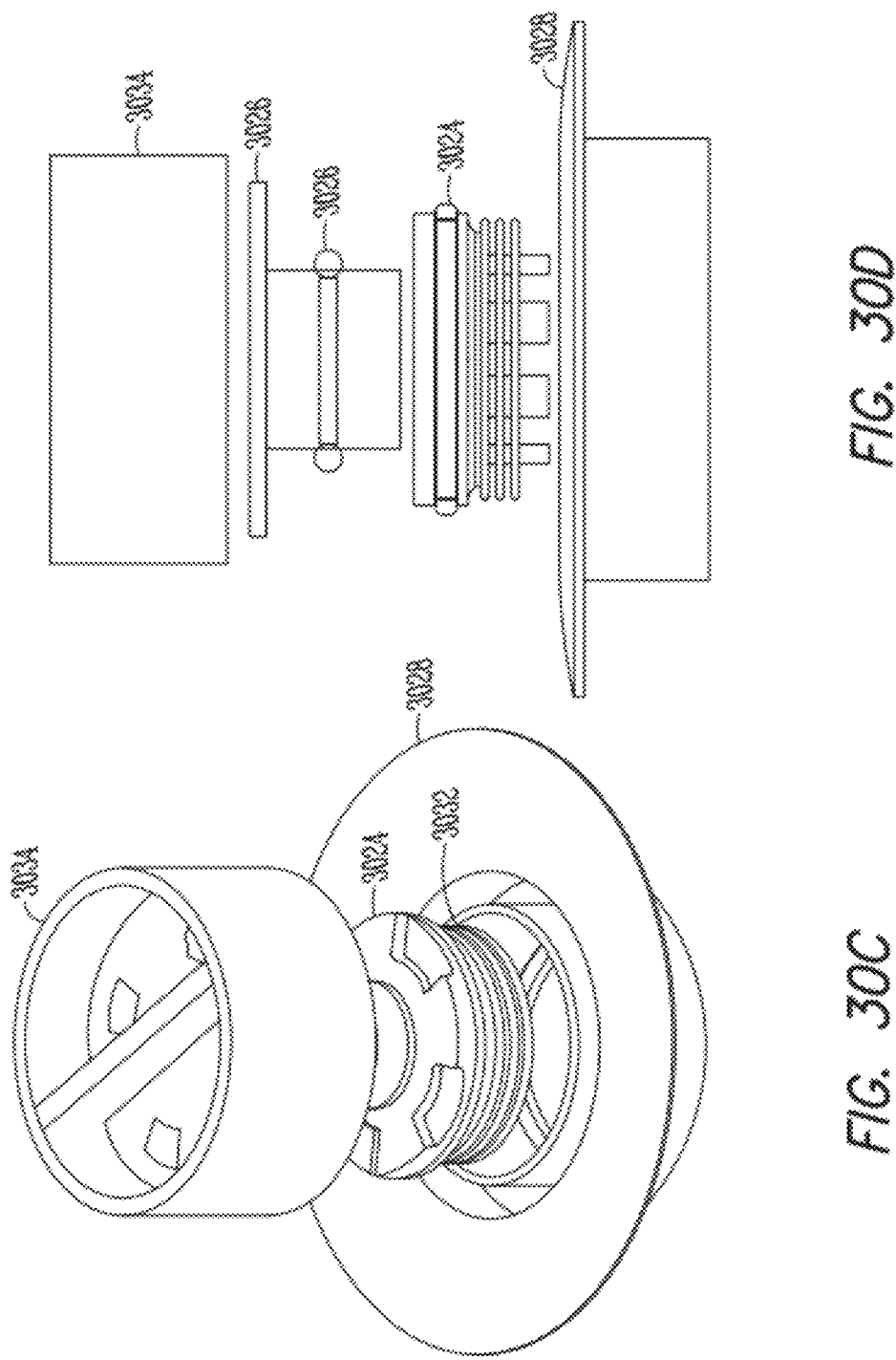

ELECTROMAGNETIC THERMAL THERAPY

CROSS-REFERENCE TO RELATED APPLICATION

This application is a continuation-of-part of commonly assigned Sham et al. U.S. Pat. No. 8,768,454, entitled "Electromagnetic Thermal Therapy," which is a continuation-in-part of commonly assigned Gill et al. U.S. Pat. No. 7,783,348, entitled "STIMULATION DEVICE FOR TREATING OSTEOARTHRITIS," filed on Apr. 16, 2008, which claims priority to Gill et al. U.S. Patent Application Ser. No. 60/927,354, entitled "STIMULATION DEVICE FOR TREATING OSTEOARTHRITIS," filed on May 3, 2007, and to Gill et al. U.S. Patent Application Ser. No. 60/983,653, entitled "STIMULATION DEVICE FOR TREATING OSTEOARTHRITIS," filed on Oct. 30, 2007, each of which are hereby incorporated by reference in their entirety.

BACKGROUND

Osteoarthritis, also known as degenerative joint disease, is characterized by gradual loss of hyaline cartilage and, in extreme cases, cyst formation in and deformation of the subchondral bone. The hyaline cartilage lines the articular surfaces of the knee and provides cushion and lubrication for the joint. During osteoarthritis, the extra-cellular matrix of the cartilage is worn down at a greater rate than it is being synthesized, leading to a net reduction in the overall amount of cartilage at the articular surfaces of the knee. As the cartilage breaks down, symptoms such as pain, swelling, tenderness, stiffness, and eventual muscle atrophy are manifested. Chondrocytes, the cellular component of hyaline cartilage that is responsible for matrix synthesis and turnover, are also depleted, thus resulting in an inability to naturally recover from this disease. Additionally, cells present in osteoarthritic joints release catabolic cytokines and enzymes that suppress collagen synthesis.

To date, conventional therapies for osteoarthritis have aimed at reducing pain and the progression of joint damage in order to minimize disability and maximize quality of life. The current algorithm for the management of osteoarthritis includes diagnosing the disease, modifying patient activity, prescribing anti-inflammatory medications, injecting steroids into the knee, and as a last resort, surgery. Although this regimen does provide some benefit, it is by no means a cure all for patients with osteoarthritis.

Aside from the conventional therapies, there are currently a number of alternative therapies that may be used to treat osteoarthritis. Three of the forerunners in the non-invasive alternative therapy field include electric, static magnetic, and electromagnetic stimulation.

Electrical stimulation, such as transcutaneous electrical nerve stimulation (TENS), delivers mild electrical impulses across the skin and into regional nerves. In patients having osteoarthritis, pain impulses are transmitted to the spinal cord through small cutaneous fibers. TENS acts to stimulate large cutaneous fibers that subsequently transmit a faster impulse via C-fibers to inhibit pain signals from the small fibers. It is in this way that TENS masks the pain normally experienced by patients having osteoarthritis. It is also thought that TENS incites the secretion of endogenous opiates, the body's natural pain killers, further reducing the pain experienced by patients with osteoarthritis.

Static magnetic stimulation has also been shown to provide medically relevant benefits. Various experiments designed to induce osteoporosis, fracture, and synovitis in animals have demonstrated faster bone repair, increased bone density, and decreased joint inflammation following magnetic treatments. It is thought that magnets can affect biological processes by: decreasing the firing rate of chronic pain neurons; modifying the rate of enzyme-mediated reactions; modulating intracellular signaling by affecting the functioning of calcium channels in the cell membranes; and enhancing blood flow. All of the above may provide some therapeutic benefit with respect to the symptoms of osteoarthritis.

Additionally, electromagnetic stimulation, a modality that generates a magnetic field by sending current through a coil, may also provide medical benefits for the treatment of osteoarthritis. It has been observed that physical stress on bone causes the appearance of tiny electric currents (piezoelectric potentials) that are thought to be the mechanism of transduction of the physical stresses into a signal that promotes bone formation. In particular, studies of electrical phenomena in cartilage have demonstrated a mechanical-electrical transduction mechanism resembling those described in bone, appearing when cartilage is mechanically compressed. Generating currents within cartilage is thought to stimulate chondrocyte activity, thus promoting the synthesis of cartilage. New cartilage synthesis may work to combat the degeneration seen in osteoarthritis and therefore alleviate the symptoms of osteoarthritis.

Thus, there is a need for an improved device and method to treat osteoarthritis.

OVERVIEW

In various embodiments disclosed herein, devices or methods for the treatment of osteoarthritis are disclosed. More particularly, certain embodiments relate to portable, disposable pulsed electromagnetic field (PEMF) stimulation and thermal therapy devices for treating osteoarthritis and their methods of use.

A portable, non-invasive device comprised of a multiple usage cuff and two single-use therapy units is designed to provide Electro-Magnetic Thermal Therapy ($EMT^2$) for treating knee osteoarthritis. The $EMT^2$ provides both transcutaneous pulsed electromagnetic field stimulation and thermal therapy. For purposes of this application, it is understood that "thermal therapy" means any therapy that provides for application of heat or cold for purposes of treatment. The $EMT^2$ is designed to alleviate pain and increase range of motion without requiring direct skin contact to the afflicted joint. The single-use therapy units offer heat or cooling and PEMF stimulation when inserted into the cuff, which provides the power and control for the coils. The cuff may contain a rechargeable power source capable of delivering a recommended amount of therapy and the coils for delivering the PEMF stimulation. The cuff may be fastened to the knee in a manner that directs the therapy to the medial and lateral areas of the joint. Furthermore, the cuff may be designed such that it is aesthetically pleasing and comfortable to wear during daily activities either over or underneath clothing, thereby increasing patient compliance.

The basic principle behind the concept of electromagnetic stimulation is that passing an electric current through a coil winding structure will generate an electromagnetic field. The electromagnetic field can, in turn, generate a current in any conductive material, such as nerves or other body tissues, within this field. The electromagnetically induced electric field created by properly oriented pulsed electromagnetic stimulation thus accomplishes the result of transferring charge to cells of the body. This induced current can lead to nerve firing, muscle contraction, stimulation of cell signaling pathways causing cell growth, and a number of other effects. In contrast to applications of electrical stimulation, pulsed electromagnetic stimulation does not require direct skin contact to induce nerve excitation. As a result, significantly higher levels of directed stimulation can be achieved through pulsed electromagnetic stimulation without the adverse effects of other technologies.

Thus, the EMT$^2$ devices and methods disclosed herein are designed with a powerful electromagnetic stimulating means created for the purpose of stimulating nerve, muscle, and/or other body tissues. Previous clinical studies have shown a high correlation between low-frequency PEMF and new cartilage growth for treating osteoarthritis. The inventive device provides an easy-to-use, portable system that may have applications within a host of clinical and home health applications.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 17A is a front view of a housing, according to an example.

FIG. 17B is a right side view of the housing of FIG. 17A.

FIG. 17C is a back side view of the housing of FIG. 17A.

FIG. 17D is a cross section side view of the housing of FIG. 17A taken at line 17D-17D in FIG. 17E.

FIG. 17E is a left side view of the housing of FIG. 17A.

FIG. 17F is a cross-section side view of the housing of FIG. 17A taken at line 17D-17D in FIG. 17C.

FIG. 17G is a bottom view of the housing of FIG. 17A.

FIG. 17H is a cross-section of a top view of the housing of FIG. 17A taken at line 17H-17H in FIG. 17C.

FIG. 17I is a top view of the housing of FIG. 17A.

FIG. 18A is a cross section of the component of FIG. 18B, taken along line 18A-18A, according to an example.

FIG. 18B is a front view of a thermal therapy component including a thin lanyard, according to an example.

FIG. 18C is a top view of the component of FIG. 18B.

FIG. 25A is a partial view of a cuff with the thermal therapy component attached via hook-and-loop, according to an example.

FIG. 25B is a cross section of the component of FIG. 25A, taken along line 25B-25B, according to an example.

FIG. 26 is a partial view of a cuff with a heat conductive pouch, according to an example.

FIG. 27 A is a perspective view of a thermal therapy component including a pod and an anchor, according to an example.

FIG. 27B is a perspective view of a thermal therapy component assembly deployed, according to an example.

FIG. 30C is a perspective view of a spool operable in the assembly of FIG. 30A.

FIG. 30D is a side view of the spool of FIG. 30C, according to an example.

DETAILED DESCRIPTION

A device for providing therapeutic treatment to a body part such as a joint to promote healing of the body part comprises a signal generator for generating a pulsed electromagnetic field based upon a selected treatment mode, a controller for storing the treatment mode and communicating the treatment mode to the signal generator, a heat source configured to provide thermal therapy to the body part, and monitoring means for monitoring the electromagnetic field generated by the electromagnetic stimulating means. The device may also include telemetry means in communication with the monitoring means for remotely accessing the controller to modify the treatment mode. The device can also be disposable.

Figure 1:
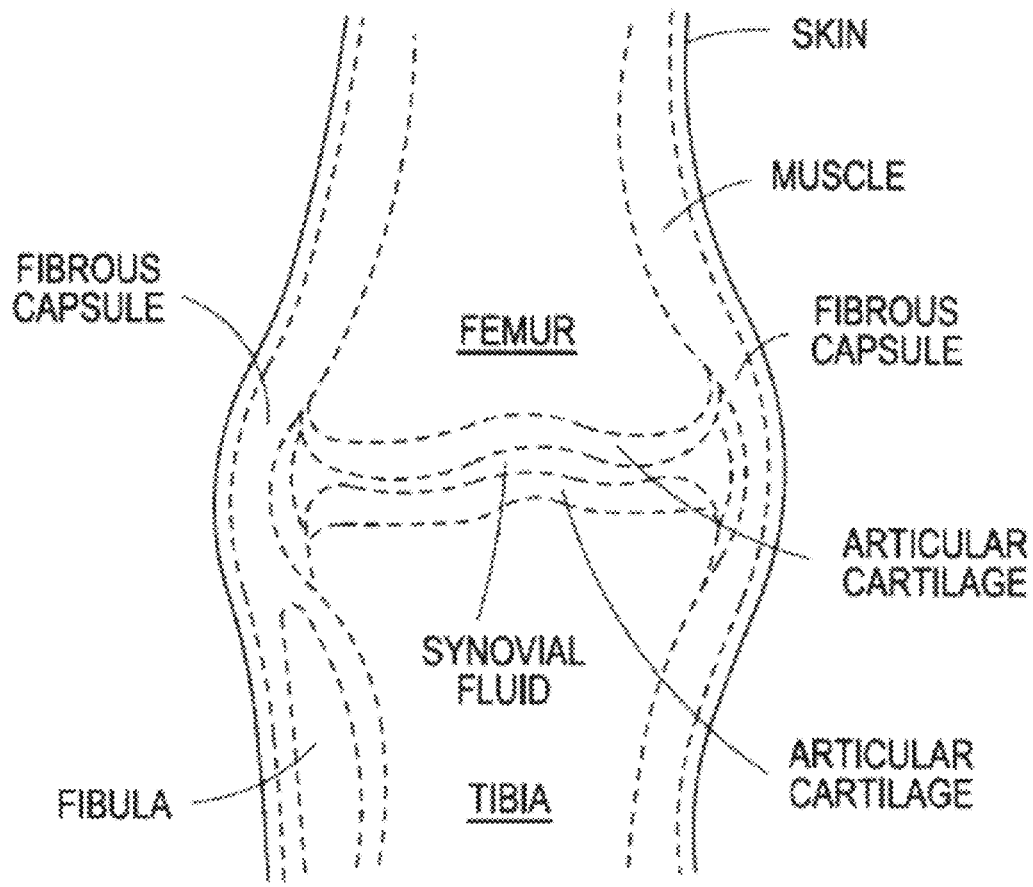
FIG. 1 is a diagram illustrating a typical human knee joint model.

FIG. 1 is a diagram illustrating a typical human knee joint model. As shown in FIG. 1, the typical human knee joint includes a compartment filled with synovial fluid that is bounded by articular cartilage on the ends of the femur and tibia, respectively, and fibrous capsules. In accordance with one embodiment of the devices and methods discussed herein, osteoarthritis in the knee joint may be treated by the application of heat or cold and specific and selective electromagnetic fields via coils positioned adjacent to the knee joint. As will be discussed in more detail to follow, a signal generator means may provide the appropriate signals to the coils for generating the specific and selective electromagnetic fields. The specific and selective electromagnetic field needed to treat osteoarthritis in the knee joint may be calculated, and varies depending upon, among other factors, the dimensions of the tibia and femur and the severity of the symptoms. Furthermore, a heating or cooling source may also be positioned adjacent to the knee joint to relieve pain, reduce patient discomfort, and increase range of motion. The heating or cooling source can also be referred to as a "thermal exchange component," which, for purposes of the instant application, means any component or device that can be used to apply heat (or any temperature that is higher than the patient's body temperature or the ambient temperature) or cold (or any temperature that is lower than the patient's body temperature or the ambient temperature).

More particularly, the implementations discussed herein relate to devices and methods for generating both (1) heat or cold, and (2) selective pulsed electromagnetic fields for the treatment of diseased tissue in a joint, such as a knee joint. The devices, which may be designed in numerous forms such as a knee brace or a small dermal patch, preferably offer transcutaneous stimulation for treating osteoarthritis. The devices may be designed to provide stimulation directly to the afflicted joint to alleviate pain and increase range of motion.

As will be discussed in further detail in subsequent paragraphs, the various $EMT^2$ stimulation device embodiments may be designed to attach to a patient for a prolonged period of time while having little disruption to daily activities and minimal skin irritation. In addition, the stimulation devices may be designed such that it is aesthetically pleasing and comfortable to wear. As a result of these and other design characteristics, patient refusal of treatment due to discomfort (i.e., patient "non-compliance") may be minimized.

Pulsed electromagnetic fields generate small, induced currents (Faraday currents) in the highly conductive extracellular fluid, which thereby mimics endogeneous electrical currents. The endogeneous electrical currents are due primarily to movement of fluid containing electrolytes in channels of the bone containing organic constituents with fixed negative charges, generating what are called "streaming potentials." Studies of electrical phenomena in cartilage have demonstrated a mechanical-electrical transduction mechanism that resembles those described in bone, appearing when cartilage is mechanically compressed, causing movement of fluid and electrolytes over the surface of fixed negative charges in the proteoglycans and collagen in the cartilage matrix. These streaming potentials serve a purpose in cartilage similar to that in bone, and, along with mechanical strain, lead to signal transduction that is capable of stimulating chondrocyte synthesis of matrix components.

In contrast to direct currents, PEMFs are able to penetrate cell membranes and either stimulate them or directly affect intracellular organelles. As a result, the effect of PEMFs on extracellular matrices includes increased synthesis of cartilage molecules, thereby enabling a "remodeling" of the knee joint.

Figure 2:
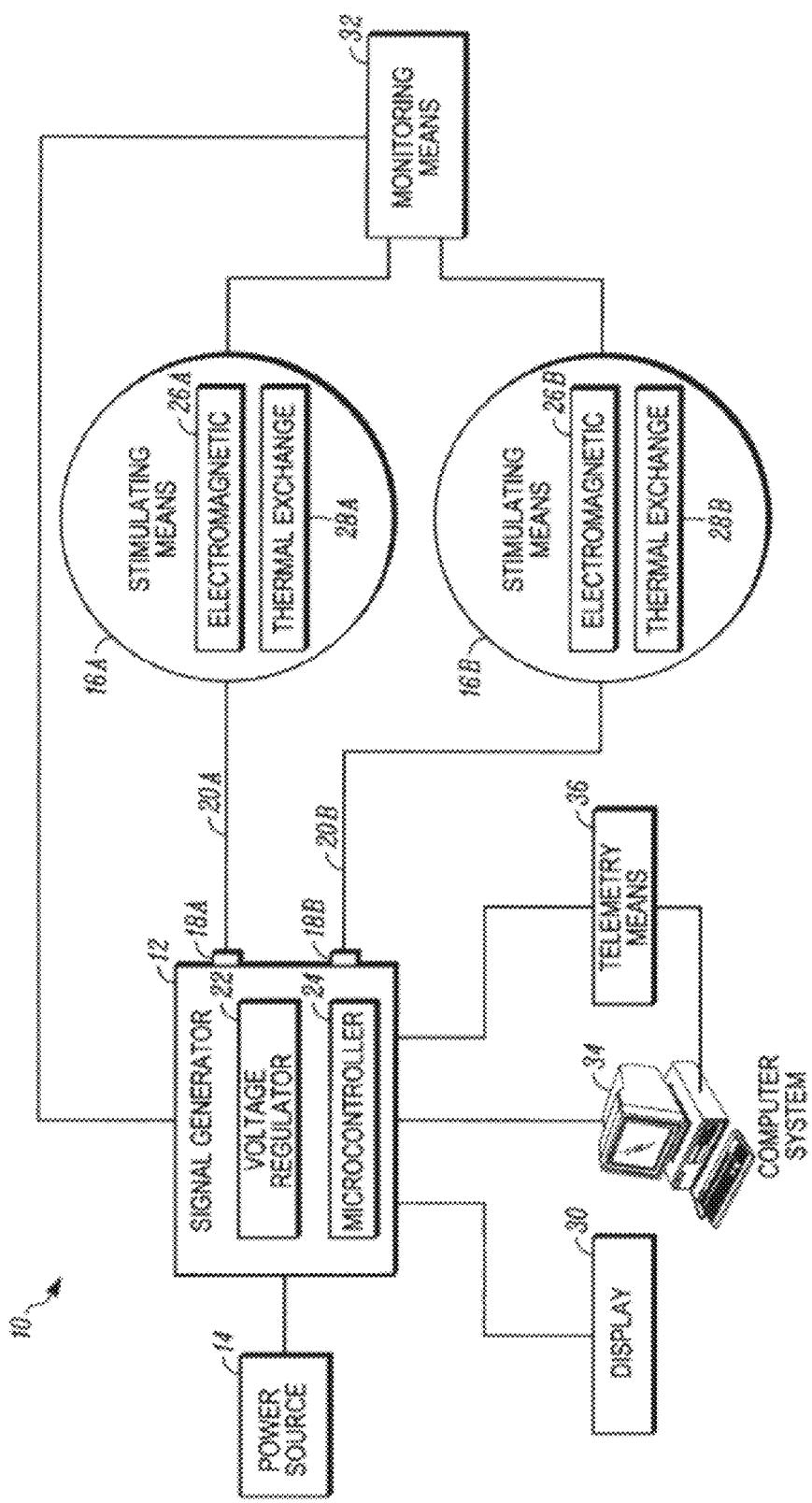
FIG. 2 is a block diagram illustrating a stimulation device for treating osteoarthritis in the knee according to one embodiment.

FIG. 2 is a block diagram illustrating $EMT^2$ stimulation device 10 for treating osteoarthritis in the knee according to one embodiment. This device embodiment 10 has a signal generator 12, power source 14, first stimulating means 16A, and second stimulating means 16B. First stimulating means 16A is coupled to first output 18A of signal generator 12 via first signal line 20A. Similarly, second stimulating means 16B is coupled to second output 18B of signal generator 12 via second signal line 20B. In various embodiments, the first stimulating means 16A has either or both of an electromagnetic stimulating means 26A and a thermal exchange component 28A and the second stimulating means 16B has either or both of an electromagnetic stimulating means 26B and a thermal exchange component 28B.

First and second signal lines 20A and 20B are configured to deliver the signals generated by signal generator 12 to create the appropriate therapeutic stimulation via first and second stimulating means 16A and 16B. First and second signal lines 20A and 20B may be "wired," such as with coaxial cable. Alternatively, a "wireless" connection means, such as Bluetooth, may be used.

Although stimulation device 10 is shown as having two output ports 18A and 18B for simultaneously and independently delivering output signals (either the same or different signals) to two stimulating means 16A and 16B, one skilled in the art will appreciate that the number of output ports and stimulating means may be varied without departing from the intended scope of the implementations disclosed herein. Thus, embodiments of device 10 that include any number of stimulating means are contemplated. For example, in one alternative embodiment, the device can have one stimulating means.

Power source 14, which may be, for example, a lithium battery pack, is provided for delivering a current input to signal generator 12. While shown in FIG. 2 as a remote unit, power source 14 may be incorporated as part of or housed together with signal generator 12. Since the embodiments may be designed with low power requirements, power source 14 may be one capable of providing an average power input of less than about 300 mW per session. As a result, power source 14 is generally small and lightweight. In an alternative embodiment, the device 10 has two power sources—one to supply power to the signal generator and another to supply power to create the thermal exchange.

As shown in FIG. 2, signal generator 12 may include voltage regulator 22 and microcontroller 24. Furthermore, first stimulating means 16A may include first electromagnetic stimulating means 26A and first thermal exchange component 28A, while second stimulating means 16B may include second electromagnetic stimulating means 26B and second thermal exchange component 28B. In one embodiment, the first and second electromagnetic stimulating means 26A, 26B are first and second coils 26A, 26B. Voltage regulator 22 may be used to provide various required supply voltages to first and second electromagnetic stimulating means 26A and 26B. First and second electromagnetic stimulating means 26A and 26B may be triggered by microcontroller 24, which may be designed to generate accurate pulses at a particular triggering and switching frequency. Output signals are delivered from microcontroller 24 to first and second stimulating means 16A and 16B, each of which is individually responsive to the signals to create a pulsed electromagnetic field.

As shown in FIG. 2, alternative embodiments of the device 10 may further include display 30 and monitoring means 32. Display 30 may be designed to display many different treatment parameters, including but not limited to a treatment mode, a power level, and an amount of time remaining in a treatment session.

Monitoring means 32 may be designed for monitoring one or more of the output conditions of stimulation device 10. In particular, monitoring means 32 may be configured to ensure that accurate treatment dosages are delivered through first and second stimulating means 16A and 16B to the patient's knee. One condition that may be monitored by monitoring means 32 is the electromagnetic field generated by first and second coils 26A and 26B. In particular, monitoring means 32 may include circuitry to both detect the strength of the electromagnetic field and adjust the signals delivered to the coils if the sensed field is not in accordance with the desired treatment level. A second condition that may be monitored by monitoring means 32 is tissue temperature generated by first and second thermal exchange component 28A and 28B. If, for example, monitoring means 32 senses a tissue temperature that is out of an acceptable range and poses a danger of injuring tissue around the knee, monitoring means 32 may communicate with the patient through display 30 to instruct removal of device 10 from the patient's knee.

For example, in one embodiment, monitoring means 32 may include a signal detector coupled to first stimulating means 16A and/or second stimulating means 16B for measuring the energy emission from first and second coils 26A and 26B. The signal detector may be designed so as to transmit a feedback signal to signal generator 12 for controlling the energy output. The actual electromagnetic energy field, or treatment dosage, that is transmitted from first and second stimulating means 16A and 16B may be measured directly by embedding the signal strength detector within the stimulating means. The signal level measured by the signal detector may then be sent to signal generator 12, where it may be used as a feedback control signal to control the output signals of the generator. If, at any time, monitoring means 32 detects a field strength outside of the desired range of the treatment mode, display 30 may display an audible, visible, tactile, or other type of alarm to inform the patient and/or physician of a malfunction in the treatment mode. Furthermore, if the measured field strength is at or above a level that poses a risk of danger, the feedback circuit of monitoring means 32 may stop the treatment to ensure that the patient is not harmed. As will be appreciated by one skilled in the art, monitoring means 32 may alternatively or additionally include a temperature sensor and associated feedback control to sense and control tissue temperature around the patient's knee.

As shown in FIG. 2, device 10 may be connected to a computer system 34 to allow the physician to program treatment modes into microcontroller 24. In this manner, the physician retains control over the type of treatment that the patient receives since device 10 may be designed such that only the physician is able to access and modify the programmed treatment modes. Through computer system 34, the physician may also monitor the treatment conditions to ensure that, for example, the correct field strength is being generated.

In order to make treatment with stimulation device 10 more convenient for both the physician and the patient, telemetry means 36 may be incorporated into the device. In general, telemetry allows for the remote measurement and reporting of information of interest to a remote system or operator. In addition, telemetry allows for the remote operation and control of a device by allowing the operator to remotely send instructions to or program the device.

With respect to stimulation device 10, telemetry means 36 enables the physician to remotely monitor the treatment as well as modify the treatment modes programmed into microcontroller 24. In this way, the physician has the ability to control and prescribe treatment modes without the requirement of a face-to-face consultation with the patient, thus making treatment of osteoarthritis more convenient for both the patient and the physician. In one embodiment, telemetry means 36 may operate using wireless communication, such as by utilizing a radio frequency (RF) system to implement the data link between the device and remote system. However, telemetry means 36 may alternatively transfer data over other media, such as a telephone line, a computer network, or via an optical link.

Figure 3:
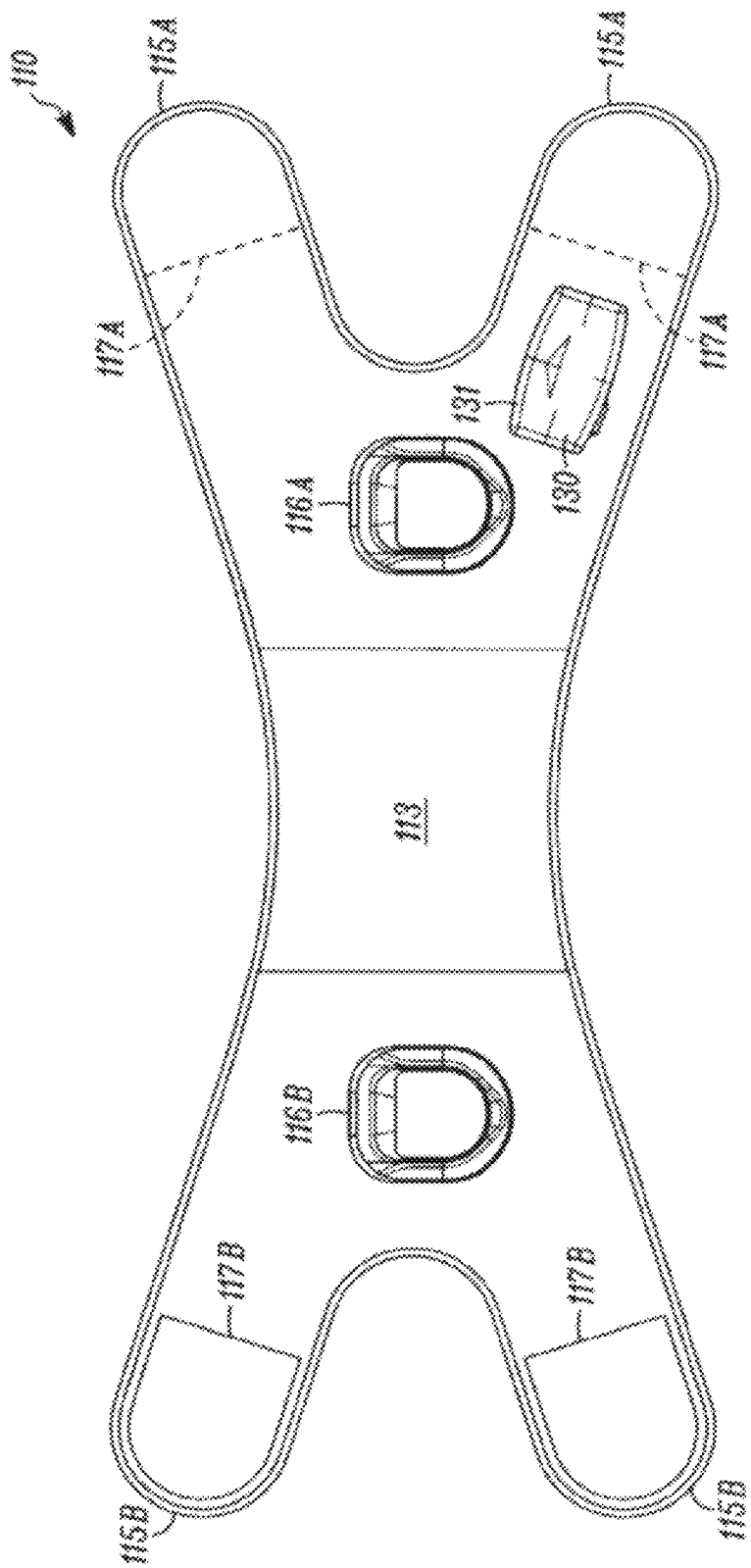
FIG. 3 is a front view of one embodiment of a stimulation device that is securable to a patient's knee for delivery of electromagnetic and thermal therapy.

Now that certain embodiments of the $EMT^2$ stimulation device have been generally described in reference to the block diagram illustration of FIG. 2, one exemplary embodiment of a stimulation device that may be worn by a patient for the treatment of osteoarthritis will be described. In particular, FIG. 3 illustrates a stimulation device 110, which generally includes a knee cuff 111, a housing 131 in which a signal generator and a power source are positioned, a first stimulating means 116A, a second stimulating means 116B, and a fastening means 117. The housing 131 can be positioned any where on the cuff 11. The device 110 alternatively also has a display 130 that can display one or more treatment parameters, such as the treatment mode or the amount of treatment time remaining in a therapy session. In the embodiment depicted in FIG. 3, the display 130 is located on the housing 131. Alternatively, the display 130 can be positioned in any location from which the display is visible to the user during use. Stimulation device 110 is a device for providing electromagnetic field stimulation and thermal therapy to a patient's body to promote healing. In particular, stimulation device 110 may provide pulsed electromagnetic field stimulation and thermal therapy (via first and second stimulating means 116A and 116B) to a knee joint suffering from the effects of osteoarthritis to promote healing of the knee. However, one skilled in the art will appreciate that various device embodiments disclosed herein may be useful to provide electromagnetic field stimulation and thermal therapy ($EMT^2$) to various other locations on a patient's body to promote healing or provide a therapeutic effect.

Knee cuff 111 includes main body portion 113, first set of strap members 115A, and second set of strap members 115B. First set of strap members 115A include first fastening members 117A, while second set of strap members 115B include second fastening members 117B. As will be discussed in the following paragraphs, first fastening members 117A are configured to mate with second fastening members 117B in order to removably couple first set of strap members 115A to second set of strap members 115B and thus, to secure knee cuff 111 to the patient's knee.

Figure 4A:
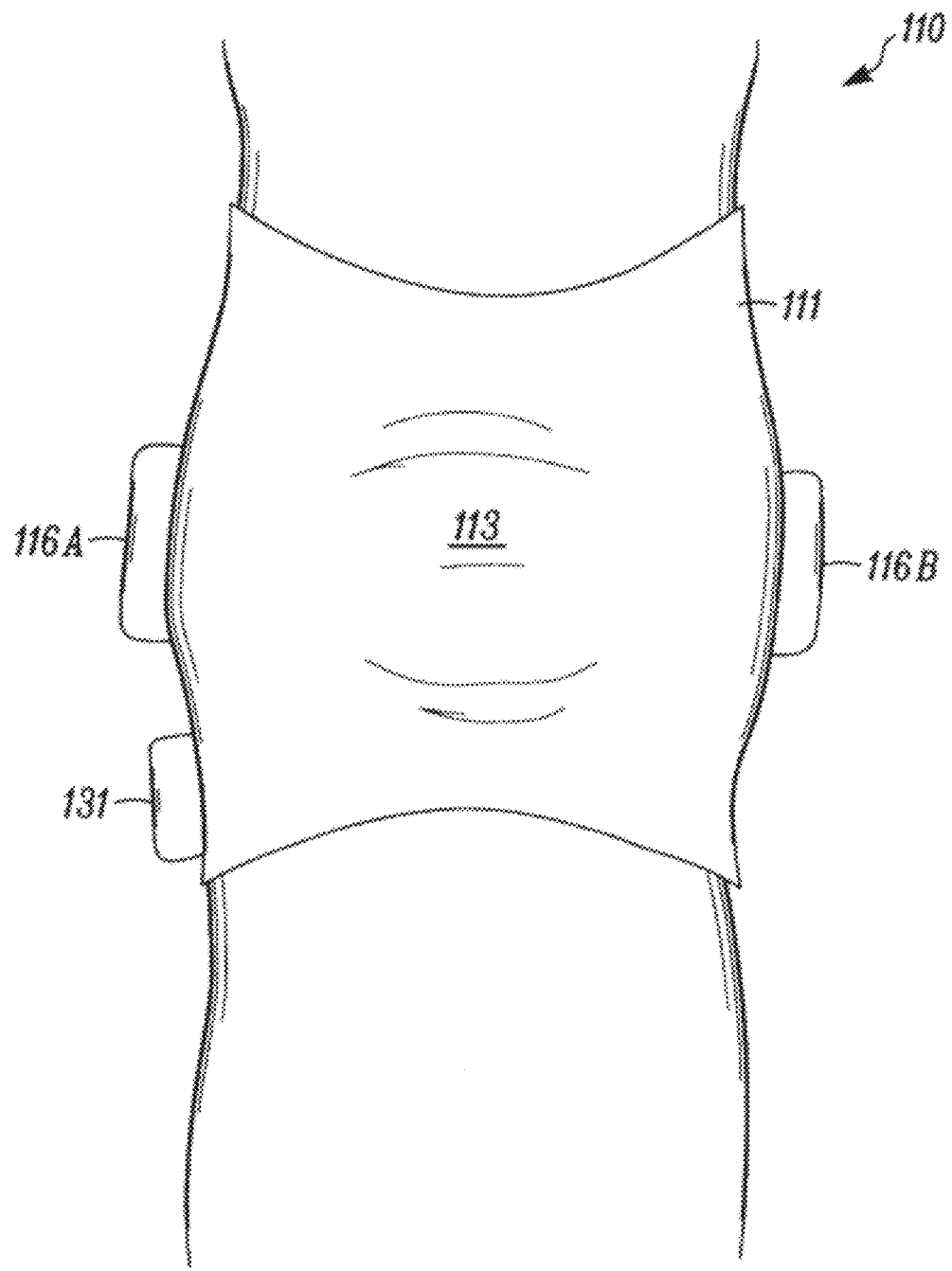
FIGS. 4A and 4B illustrate the stimulation device of FIG. 3 secured to the patient's knee.
Figure 4B:
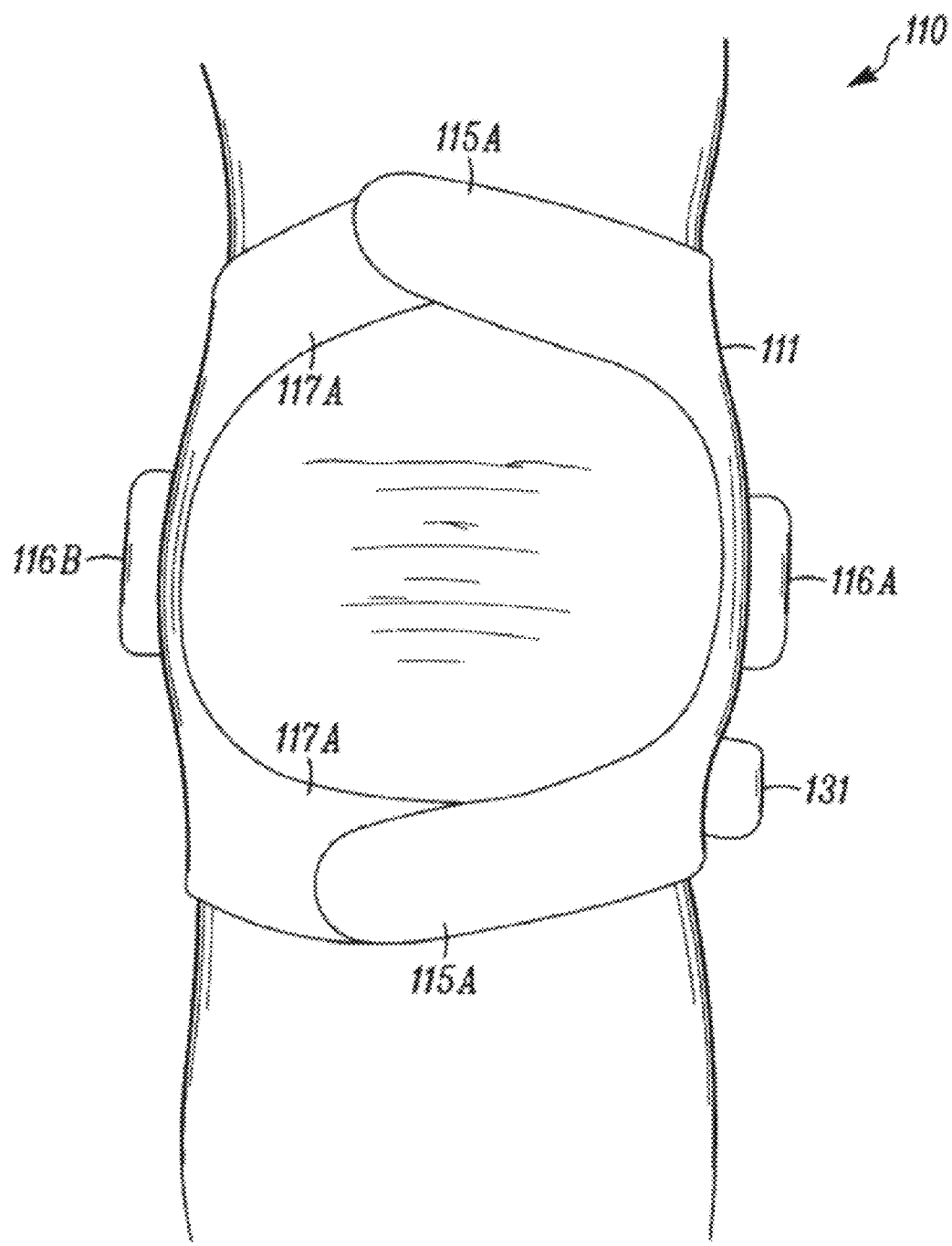

FIGS. 4A and 4B illustrate stimulation device 110 secured to the patient's knee, according to one embodiment. In particular, FIG. 4A illustrates a front side of the patient's knee, while FIG. 4B illustrates a back side of the knee. Knee cuff 111 of stimulation device 110 is wrapped around the knee such that first set of strap members 115A having first fastening members 117A overlap with second set of strap members 115B having second fastening members 117B to secure the cuff at the desired location on the knee. When properly secured to the knee, first stimulation means 116A is positioned at a lateral knee location, while second stimulating means 116B is positioned at a medial knee location. In one embodiment, first fastening members 117A and second fastening members 117B form a hook-and-loop fastening means, such as that commonly known as VELCRO®, wherein first fastening members 117A are the "hook" portions and second fastening members 117B are the "loop" portions. However, other means of fastening may be used including, but not limited to, buckles, snaps, and zippers. In alternate embodiments of knee cuff 111, no fastening means is used. Instead, the fabric forming the wrap is capable of being stretched and is able to hold itself in place due to the elasticity of the wrap.

Figure 5:
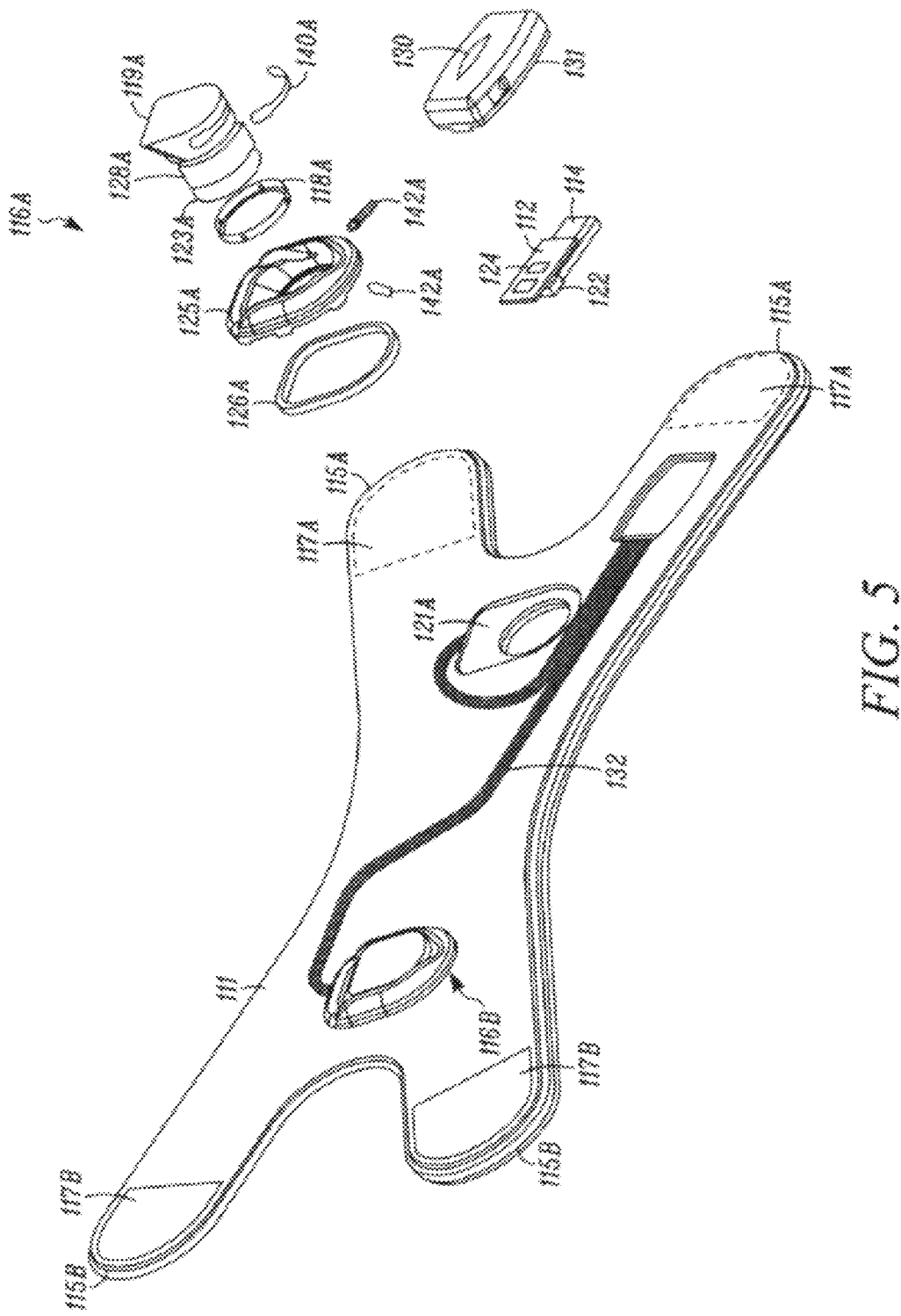
FIG. 5 is an exploded perspective view of the stimulation device of FIG. 3.

FIG. 5 is an exploded perspective view of stimulation device 110 according to a further embodiment. As shown in FIG. 5, first stimulating means 116A includes first coil 126A, first stimulating means holder 125A, first stimulating means holder base plate 121A, first thermal exchange component 128A, and first stimulating means housing 119A. First coil 126A of first stimulating means 116A is designed to be contained within the first stimulating means holder 125A. The first stimulating means holder base plate 121A provides a base for the first stimulating means holder 125A to attach to in order to be joined to the knee cuff by means of any one of such exemplary attachment mechanisms as, but not limited to, an irreversible snap-fit hook mechanism, ultrasonic welding, or glue. In one embodiment, the first stimulating means holder base plate 121A may be permanently attached to the knee cuff 111 by sewing, glue, or any known attachment means. First thermal exchange component 128A is designed to be contained within first thermal stimulating means housing 119A. Housing 119A. Housing 119A may then be enclosed on a back side by a thin plastic barrier 123A formed from a material such as Tyvek®. The thin barrier 123A can be attached to the housing 119A by glue, heat seal, or a plastic snap-fit cover 118A. First thermal exchange component 119A is insertable into first stimulating means holder 125A, which is coupled to knee cuff 111 as shown in the embodiment depicted in FIG. 3.

Although not shown in an exploded view like first stimulating means 116A, second stimulating means 116B includes similar components in a similar configuration. Thus, the discussion focuses on first stimulating means 116A for purposes of example only, but applies equally to second stimulating means 116B. As a result, second stimulating means 116B includes similar components having similar reference numerals.

The signal generator 112 depicted schematically in FIG. 5 includes a voltage regulator 122 and a microcontroller 124, which control the signals transmitted through the wire harness 132 to first and second coils 126A and 126B to provide the pulsed electromagnetic field to the knee. The wire harness 132 is hidden within the different fabric layers of the knee cuff 111. Power source 114, which provides power to voltage regulator 122, is positioned in the same housing that contains the signal generator means 112. However, as discussed above, power source 114 may alternatively be positioned remotely from the signal generator means 112. In a further alternative embodiment, two power sources are provided: one for the signal generator and one for the thermal exchange component. In yet another embodiment, three power sources are provided: one for the signal generator and one for each of the thermal exchange components. In one embodiment, the power sources for the thermal exchange components are single-use heating mixtures that provide energy when exposed to air.

First and second coils 126A and 126B are either unipolar or bipolar electromagnets that generate a magnetic field when electrical current flows through them. The magnetic field is created by passing an electric current through first and second coils 126A and 126B, which are preferably formed from a long wire strand coiled around a core. The "pulsed" electromagnetic field may be created by programming microcontroller 124 to turn the electromagnetic field on and off at a rapid rate.

Although first and second thermal exchange components 128A and 128B are not required components, incorporating them into first and second stimulating means 116A and 116B, respectively, may provide beneficial treatment results. In particular, when used in combination with electromagnetic therapy, thermal therapy is helpful in treating the effects of osteoarthritis and improving patient compliance. However, one skilled in the art will appreciate that embodiments of stimulation device 110 that apply only thermal therapy, only electromagnetic therapy, or a combination of both therapies are possible. As a result, the stimulation devices described herein may be tailored to the particular needs of different patients.

Heat is a natural remedy that may be used to both relieve pain and reduce discomfort. This is accomplished by stimulating the patient's thermoreceptors which, in turn, aid in blocking the pain sensation from reaching the brain by relaxing deep muscles to reduce tenderness and pain. In order to attain a therapeutic heat transfer effect including increases in tissue temperature, blood flow, muscle lengthening, and metabolism, an intramuscular temperature of about 104 degrees F. (40 degrees Celsius) must be reached.

Numerous types of heat sources may be utilized to provide beneficial heat therapy in accordance with various implementations. For example, first and second thermal exchange components 128A and 128B may be multi-use cartridges that require the patient to 're-heat' the cartridges before every use, such as by placing the cartridges in the microwave. Alternatively, first and second thermal exchange components 128A and 128B may be one-time use cartridges that are designed to provide an irreversible exothermic reaction to provide a source of heat for a specified amount of time. In one embodiment, first and second thermal exchange components 128A and 128B are cartridges that contain iron, carbon, sodium chloride, sodium thiosulfate, and water. When the CLLHW compound is exposed to air, it undergoes an exothermic reaction that produces heat. In other embodiments, heat may be provided through: a resistive based heating source; selective insulation; or "warmth" radiated from the battery during operation. As will be appreciated by one skilled in the art, first and second thermal exchange components 128A and 128B may be heat sources designed such that they deliver heat therapy for any designated period of time ranging from a few minutes to the entire day. This designated period may or may not coincide with the electromagnetic field duration. In addition, first and second thermal exchange components 128A and 128B may be pulsed such that the heat therapy is not constant.

In one embodiment, power source 114 is a lithium-polymer battery, which may be either a single-use battery or a rechargeable, multi-use battery. If power source 114 is a rechargeable type battery, stimulation device 110 may be configured for attachment to a docking station for recharging the device. Alternatively, the docking station may be designed to receive only power source 114, which may be made removable from stimulation device 110. As one skilled in the art will appreciate, numerous other types of power sources may be used to provide the requisite power to stimulation device 110. For example, stimulation device 110 may be designed to create power from the patient's body movements. Alternatively, stimulation device 110 may be powered through a chemical reaction with heat being the by-product. In this case, the heat by-product may provide the heat therapy to the knee joint.

As shown in FIG. 5, stimulation device 110 further includes display 130 for displaying one or more treatment parameters, such as the treatment mode or the amount of treatment time remaining in a therapy session. Display 130 may utilize many different types of indicator means such as, for example, a light source, a heat-sensitive material that changes color (as a function of elapsed time), a digital timer, or sound repetition. In addition, display 130 may function together with a monitoring means in order to transmit an audio, visual, or tactile-type message to the patient in response to the monitoring means sensing, for example, an electromagnetic field strength that is outside of that defined by the treatment mode. In this instance, display 130 is useful to instruct the patient to remove the stimulation device or to call his or her physician.

Figure 6:
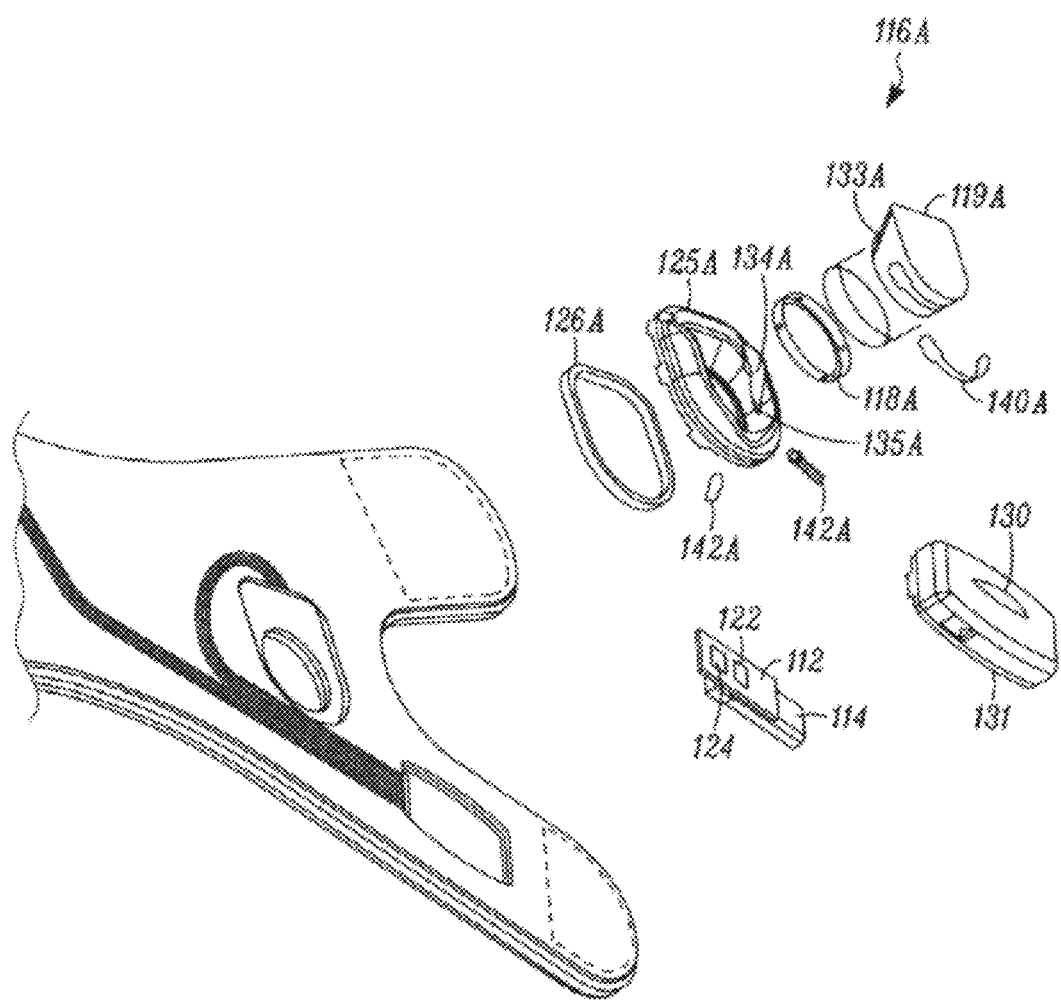
FIG. 6 is an enlarged exploded view of a portion of the stimulation device of FIG. 3.

FIG. 6 is an enlarged illustration of the exploded perspective view of FIG. 5, according to one embodiment. In this embodiment, the stimulating means housings 119A, 119B as depicted in FIG. 5 are insertable, replaceable units that can be easily and quickly inserted into and removed from the means holders 125A, 125B. In one embodiment, the stimulating means housings 119A, 119B have connections that, upon insertion into the holders 125A, 125B, couple with connections in the holders 125A, 125B to supply power to the housings 119A, 1193B.

FIG. 6 depicts one embodiment of a stimulation device 110 with insertable stimulating means housings 119A, 119B. As shown in FIG. 6, the stimulation device 110 has a metal plate 140A in the stimulating means housing 119A and a first pair of stimulating means holder spring-loaded metal contacts 142A. When the stimulation device 110 is assembled as shown in the embodiment of FIG. 3, the metal plate 140A on the stimulating means housing 119A is used to make an electrical connection with a pair of spring-loaded metal contacts 142A in the first stimulating means holder 125A. The protrusions 133A on the stimulating means housing 119A can slide in and out of the grooves 134A on the stimulating means holder 125A and engage in the notches 135A to create a reversible mechanical snap-in feature that allows for secure insertion and removal of the housing 119A to the stimulating means holder 125A. In an alternative implementation, the metal plate 140A in the stimulating means housing 119A makes contact with the first pair of stimulating means holder magnets that are inserted into a first pair of magnet notches in first stimulating means holder 125A for securing the housing 119A to the first stimulating means holder 125A. In a further alternative, instead of a metal plate, the stimulation device 110 can have a pair of stimulating means magnets and a corresponding pair of stimulating means holder magnets.

The first pair of stimulating means holder spring-loaded metal contacts 142A are coupled to a corresponding pair of signal lines (not shown) in communication with signal generator 112. When first stimulating means housing 119A is positioned within first stimulating means holder 125A, the electrical connection between the metal plate 140A and the corresponding first pair of stimulating means holder spring-loaded metal contacts 142A creates a closed circuit that electrically couples first stimulating means 116A to signal generator 112. As a result, signal generator 112 is able to communicate with first stimulating means 116A to deliver the prescribed treatment signals defined by the treatment mode programmed into microcontroller 124.

The embodiment of stimulation device 110 illustrated in FIGS. 3-6 is a two coil arrangement with one coil on either side of the knee for generating the PEMF therapy. In general, voltage regulator 122 is used to provide a constant supply voltage to signal generator 112, and first and second stimulating means 116A and 116B. Microcontroller 124 triggers first and second coils 126A and 126B, thereby generating accurate pulses at a particular triggering and switching frequency defined by the designated treatment mode stored in the microcontroller. The triggering frequency is defined as the rate at which a set number of pulses occur. The switching frequency is the fundamental frequency of the individual pulses. Another parameter called the switching duty cycle is defined as the ratio of the pulse width over the switching period. The voltage of the pulses is equivalent to the amplitude of the PEMF therapy.

The required penetration depth of the pulsed electromagnetic field generated by signal generator 112 and first and second stimulating means 116A and 116B may vary depending upon, for example, the size of the patient's knee region. However, for an adult patient, the penetration depth is generally in the range of about 1 cm to about 5 cm. Alternatively, the penetration depth is in the range of about 2 cm to about 4 cm. In a further alternative, the penetration depth ranges from about 2 cm to about 2.5 cm. This "penetration depth" parameter is necessary in order to estimate the magnetic field intensity needed to provide the therapy, which ultimately determines the power requirement of power source 114.

In general, the magnetic field intensity generated by a coil is measured in terms of Tesla (T) and has the following approximate relationship with current flowing through the coil:

$$B = \frac{\mu_0 n I R^2}{2(R^2 + x^2)^{3/2}} \Rightarrow \sqrt{\frac{2B(R^2 + x^2)^{3/2}}{\mu_0 n R^2}}$$

where "B" is the magnetic field produced by the coil, "I" is the current through the coil, "R" is the radius of the coil, and "x" is the penetration depth of the PEMF.

According to one embodiment, the magnetic field strength B applied to the target body part of the patient ranges from about 10 µT to about 2,000 µT. Alternatively, the magnetic field strength B ranges from about 20 µT to about 100 µT. In a further alternative, the magnetic field strength B ranges from about 30 µT to about 50 µF. In yet another alternative, the magnetic field strength B is about 40 µT. According to one embodiment, the magnetic field produced by the coil is applied perpendicular to the coil.

In one implementation, the magnetic field is applied into the knee for a distance ranging from about 1 cm to about 5 cm into the knee. Alternatively, the magnetic field is applied for a distance ranging from about 2 cm to about 4 cm into the knee. In a further alternative, the magnetic field is applied to a distance ranging from about 2 cm to about 2.5 cm into the knee.

The coil, in accordance with one embodiment, has 20 turns of a 24 AWG wire around a core with a radius of about 2 centimeters with a pulsed current 712 mA. Alternatively, the coil has 65 turns of a 28 AWG wire around a core with a radius of 1.5 cm with a pulsed current of 339 mA.

While a single-coil configuration is possible and within the intended scope of this application, the two-coil configuration uses about 20 times less power than the single-coil configuration because it requires a significantly smaller amount of energy to penetrate both the lateral and medial side of the knee. Furthermore, embodiments having more than two coils are also contemplated.

In one embodiment, the PEMF therapy is applied for period ranging from about 30 minutes to about 4 hours. Alternatively, the PEMF therapy is applied for a period ranging from about 1 hour to about 3 hours. In a further alternative, the therapy is applied from about 1.5 to about 2.5 hours. In yet another alternative, the therapy is applied for about 2 hours. Further, the optimal treatment window may vary depending upon many factors, including, but not limited to, the field intensity provided to the knee, the severity of the osteoarthritis in the knee, and the physical dimensions of the knee.

According to one implementation, the triggering frequency ranges from about 1 Hz to about 100 Hz. Alternatively, the triggering frequency ranges from about 5 Hz to about 50 Hz. In a further alternative, the triggering frequency ranges from about 10 Hz to about 20 Hz. In yet another alternative, the triggering frequency is about 15 Hz.

In accordance with one embodiment, the switching frequency ranges from about 50 Hz to about 100 kHz. Alternatively, the switching frequency ranges from about 300 Hz to about 70 kHz. In a further alternative, the switching frequency ranges from about 2 kHz to about 4 kHz. In yet another alternative, the switching frequency is about 3 kHz.

In general, in order to achieve the optimal therapeutic effect with the PEMF, a triggering frequency in the range of about 15 Hz and a switching frequency in the range of about 3 kHz are desirable, although other triggering and switching frequencies are also contemplated.

As one skilled in the art will appreciate based upon the above disclosure, stimulation device 110 does not require connection to any external hardware while delivering the prescribed therapy. Thus, stimulation device 110 is portable, and is designed such that it may be worn by the patient during their normal daily activities without discomfort. Knee cuff 111 may be both ergonomically designed and cosmetically appealing to increase patient compliance with wearing the device.

First and second stimulating means 116A and 116B may be designed as complete or partial disposable units that may be discarded and replaced after a predetermined number of treatments. For example, stimulating means housing 119A, which may include first thermal exchange component 128A and/or first coil 126A, may be removed from stimulation means holder 125A and disposed of by the patient upon expiration. Optionally, display 130 may instruct the patient when the units have expired and require replacement. The disposability feature of first and second stimulating means 116A and 116B may be advantageous because if one or more of the stimulating means stops functioning properly, it is only necessary to replace those components and not the entire stimulation device.

Figure 7:
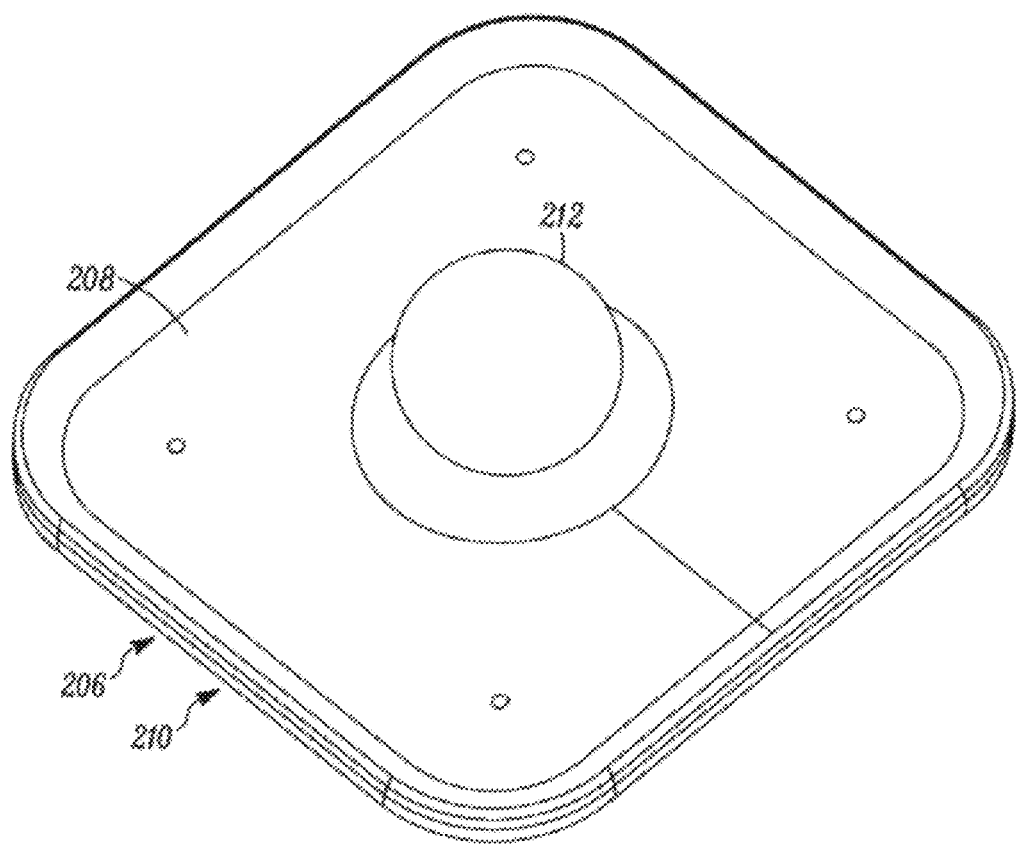
FIG. 7 is a perspective view of one embodiment of a stimulation device in the form of a patch that is securable to a patient's body for delivery of electromagnetic and thermal therapy.

Another exemplary embodiment of an $EMT^2$ stimulation device is depicted in FIG. 7. The device 200 shown in FIG. 7 has a PEMF generation component 202 and a thermal exchange component 204. The PEMF generation component 202 is positioned between a first exterior layer 206 and a second exterior layer 208. According to one embodiment, the first layer 206 has an adhesive component 210 on at least a portion of the side of the layer external to the device 200. The adhesive component 210 is any known adhesive that allows for attaching the device 200 to the patient's skin.

In accordance with one implementation, the device 200 also has a power source (not shown) positioned in an external casing 212 positioned on the second layer 208. In a further embodiment, certain electronic components can be positioned in the casing 212.

Alternatively, the device 200 has two power sources (not shown)-one for the PEMF generation component 202 and one for the thermal exchange component 204. Two different power sources can help to maximize battery life. Alternatively, one power source is provided for both the PEMF generation component 202 and the thermal exchange component 204. In a further embodiment, one power source is provided for the PEMF generation component 202, and the thermal exchange component 204 in this embodiment requires no power source, as explained in further detail below. According to one implementation, the single power source or both power sources are positioned in the external casing 212. Alternatively, the single power source or both power sources are positioned between the first layer 206 and the second layer 208. In a further alternative, one power source is positioned in the external casing 212 and one power source is positioned in between the first 206 and second 208 layers.

In one embodiment, one or both of the power sources are a single-use or disposable power source. Alternatively, the one or more power sources can be reusable or permanent power sources. In a further alternative, the power source is any known power source for use with a PEMF stimulation device and/or a thermal exchange component.

In one embodiment, the device 200 is a single-use patch-like device. Alternatively, the device 200 is a reusable device. As shown, the device 200 has a square shape. Alternatively, the device 200 can have a circular or round shape or any other known shape. For example, in one embodiment, the device 200 may have any shape that maximizes attachment to the patient's skin and patient comfort.

In this embodiment, the PEMF generation component 202 is a coil configured to generate the pulsed electromagnetic field. Alternatively, the PEMF generation component 202 can be any known component for generating a PEMF.

According to one implementation, the thermal exchange component 204 is a heat source such as, for example, a component having an exothermic chemical mixture. For example, the heat source in one embodiment is a mixture containing iron powder, water, activated charcoal, and salt that oxidizes in air to generate heat. One commercial example of such a mixture can be found in hand warming products sold by HeatMax®, which is located in Dalton, Ga. Another example of a heat source that can be used with the present embodiment is a mixture containing super-cooled sodium acetate. Yet another example is a mixture containing calcium chloride or magnesium sulfate and water. In a further alternative, the thermal exchange component can be any known component or device for generating heat.

In accordance with one implementation in which the thermal exchange component 204 is a heat source utilizing an exothermic chemical mixture, the component 204 does not require a power source. That is, the chemical mixture generates the exothermic reaction without the need for any battery or any other kind of power source.

Alternatively, the thermal exchange component 204 is a cooling source such as, for example, a component having an endothermic chemical mixture. For example, the cooling source can be a mixture containing ammonium nitrate and water. In a further alternative, the thermal exchange component 204 can be any known component for providing a temperature reduction.

In one implementation, the first and second exterior layers 206, 208 are flexible or pliable layers. The layer pliability or flexibility can, according to one embodiment, facilitate attachment of the device 200 to the patient's skin. In one alternative embodiment, one or both of the exterior layers can be gas permeable. In a further alternative, one or both of the exterior layers are permeable to oxygen. The layers 206, 208 can consist of a biocompatible membrane such as, for example, the Tegaderm™ and Medipore™ products available from 3M™ Company, located in St. Paul, Minn.

According to one embodiment, the adhesive component 210 is a hypoallergenic adhesive. In a further alternative implementation in which one or both of the exterior layers 206, 208 are gas permeable, the adhesive component 210 is a porous adhesive that allows gas to pass through the adhesive and the gas permeable layer.

It is understood that this device 200 can be used to treat any joint or any other body part that might benefit from treatment with PEMF and thermal exchange. In one embodiment, the target area is the knee. It is further understood that more than one device 200 could be used to treat a target area. The device 200 can be used to relieve osteoarthritis pain and increase range of motion.

One skilled in the art will appreciate that although the devices and methods have been described in reference to only a few embodiments of a stimulation device, these embodiments are provided for purposes of example and not limitation. Accordingly, numerous other embodiments are possible and within the intended scope.

Other Examples

Figure 8:
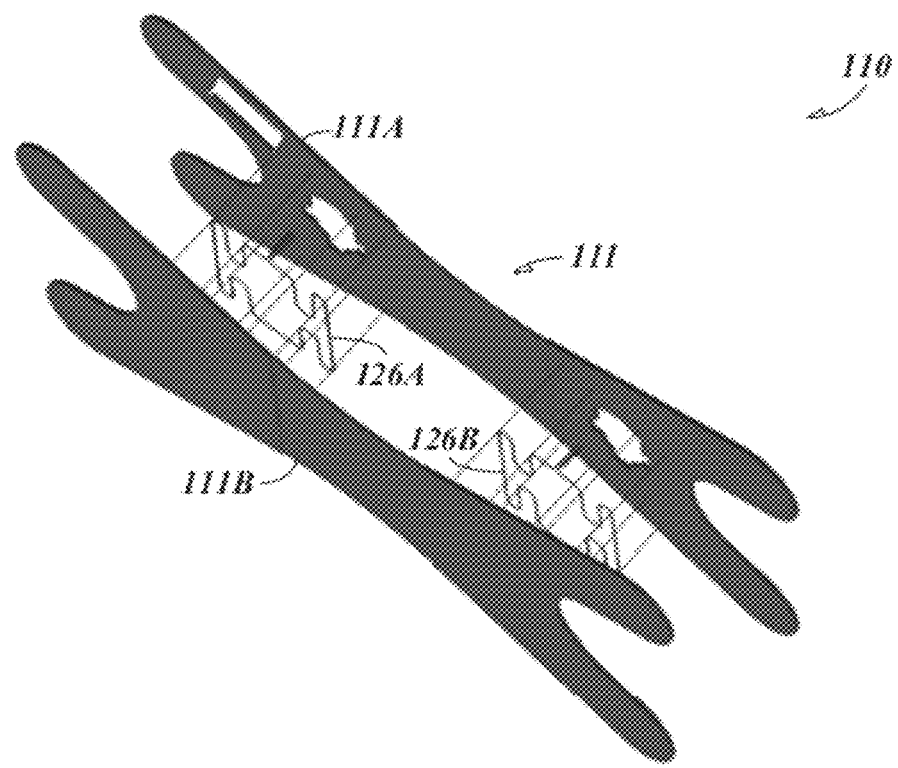
FIG. 8 illustrates generally an exploded perspective view of an active knee system.

FIG. 8 illustrates generally an example of an active knee system including a stimulation device 110, the stimulation device 110 including a knee cuff 111 having a first layer 111A and a second layer 111B. In the example of FIG. 8, the active knee system includes a portable, battery operated, non-invasive shortwave diathermy medical device that applies electromagnetic energy for the treatment of medical conditions using means other than the generation of deep heat within body tissues (e.g., using athermal means).

In an example, the active knee system can be configured to deliver a pulsed RF signal to a target tissue via inductive coupling with applicator coils (e.g., a first coil 126A and a second coil 126B). In this example, the applicator coils are placed on either side of a knee (e.g., the medial and lateral areas of the knee joint) within the knee cuff 111 (e.g., between the first layer 111A and the second layer 111B). In other examples, the applicator coils can be placed in other locations about the knee cuff (e.g., depending on the desired target tissue) or one or more applicator coils can be placed in one or more locations within one or more other cuffs configured to be placed about one or more other parts of the body.

In an example, separate RF signal generators can be located proximate each applicator coil (e.g., within a stimulation means holder, proximate an applicator coil, or in certain examples, within the same sub-assembly as the applicator coil) to significantly reduce potential RE signal degradation in comparison to a system having multiple applicator coils separately routed, in some examples, substantially large distances, to a single RF signal generator. In other examples, separate RF signal generators can be assigned to a first group of applicator coils located in closer proximity than a second group of applicator coils.

In certain examples, one or more of the RF signal generators or the applicator coils can be controlled by a single microcontroller contained within a separate housing (e.g., a housing 131) removable from the knee cuff 111 (or one or more other cuff). The microcontroller can control the RF signal generators (e.g., on-state, off-state, etc.) using a low-speed power line. The combination of the RF signal generators located proximate the applicator coils and the separate microcontroller can allow complete modularization of the system (e.g., the one or more RF signal generators or applicator coils can be placed independently from the microcontroller).

The stimulation device 110 can include one or more disposable, single-use, air activated pods that provide heat or cold to a target tissue. In an example, the one or more pods can be snapped or otherwise attached into medial and lateral slots or holders on the knee cuff 1. In various examples, treatment (e.g., PEMF therapy, or one or more of thermal therapy or electromagnetic therapy) can occur through dressings, clothing, casts, compression garments, supports, or one or more other barrier between the knee cuff 111 and the target tissue. Further, in certain examples, the pods (separately or in combination) can act as an activator switch that enables or turns on one or more portion of the PEMF therapy.

In an example, the PEMF therapy can include one or more of the following parameters: 1 W peak generator power; 4 mW average generator power; 3V generator voltage; a voltage standing wave ration of approximately 1; 10 mA current; 27.12 MHz carrier frequency; 2 msec burst duration (e.g., 2 msec burst on, and 498 msec burst off); 2 Hz burst frequency; 50 Ohm standard load; etc. In other examples, the PEMF therapy can include one or more other parameters.

Although the example of FIG. 8 illustrates generally an active knee system, one or more other systems configured to provide therapy to one or more other target areas are consistent with the teachings herein, such as an active ankle system, an active wrist system, etc.

Active Ankle System

Figure 9:
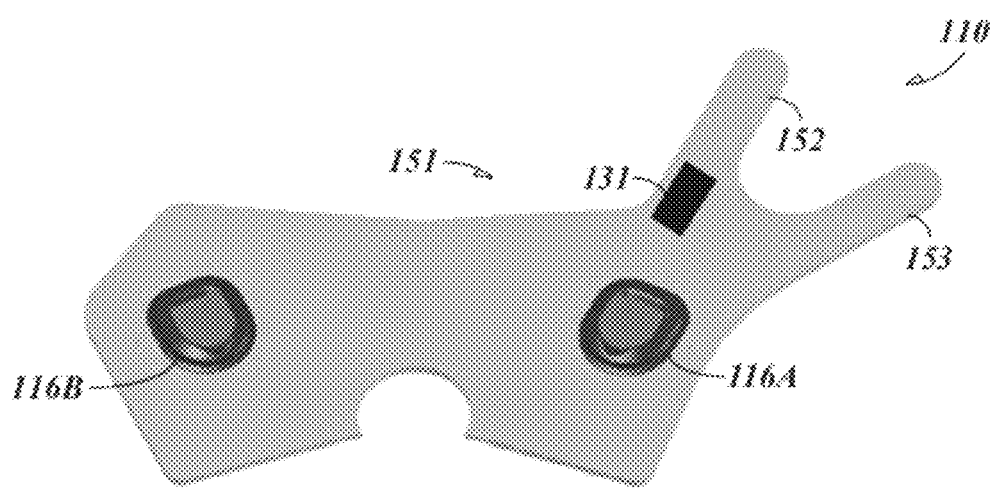
FIG. 9 illustrates generally an example of an active ankle system.

FIG. 9 illustrates generally an example of an active ankle system including a stimulation device 110, the stimulation device 110 including an ankle cuff 151 configured to be worn around an ankle, first and second stimulating means 116A, 116B configured to provide therapy to the ankle, and a housing 131 configured to store a microcontroller to control at least a portion of at least one of the first or second stimulating means 116A, 116B. In an example, the ankle cuff 151 can include fasteners, in this example, first and second straps 152, 153 configured to cross over the front of the ankle and securely fasten the ankle cuff 151 to the ankle. In an example, the fasteners can include hook and loop fasteners, or one or more other type of fastener.

The active ankle system can be configured to deliver PEMF therapy (e.g., a pulsed RF signal) to a target tissue using one or more applicator coils (e.g., first and second coils), as well as thermal therapy (e.g., heat therapy) using one or more disposable, single-use air activated pods, to a target area of the ankle. In an example, the first or second stimulating means 116A, 116B can include at least one of an applicator coil or a thermal pod. In an example, the PEMF or thermal therapies can be provided near the tibiotalar and talocalcaneal joints of the ankle, which are generally the most common places for arthritis in the ankle to occur. By positioning the applicator coils or the thermal pods at or near the tibiotalar and talocalcaneal joints of the ankle, treatment of both the commonly injured (e.g., when an ankle is rolled or sprained) posterior and anterior talo-fibular ligaments is possible.

In other examples, the PEMF or thermal therapies can be used to reduce post-surgical pain and edema in the ankle, as well as provide one or more other therapeutic benefits. Using the unique wrap design illustrated in FIG. 9, the ankle cuff 151 can be worn on either the left or right ankle and still provide therapy to the target locations of the ankle without producing different active ankle systems for each side. Further, the applicator coils or the thermal pods can be placed in one or more other locations about the ankle cuff 151 due to the modular design of the system, such as described above.

Active Back System

Figure 10:
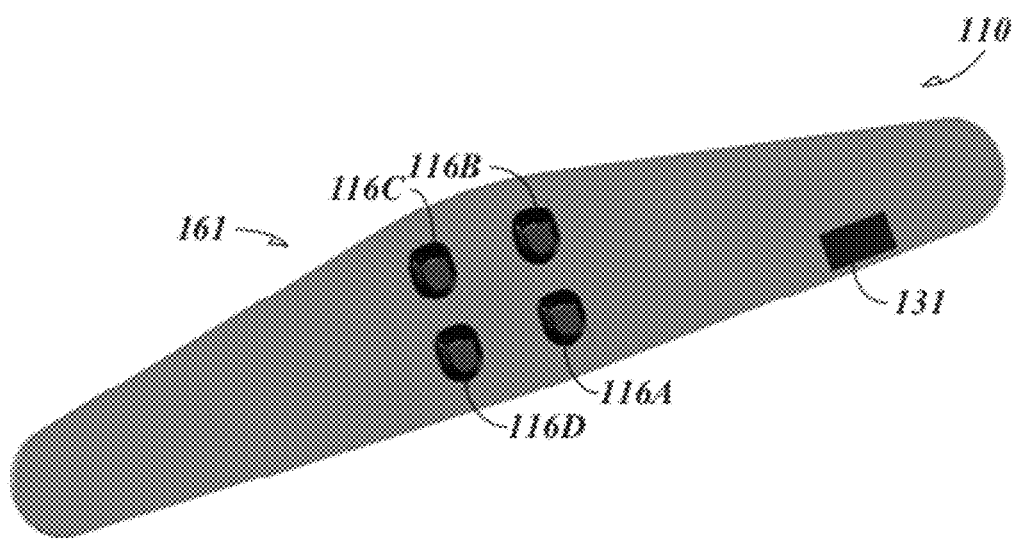
FIG. 10 illustrates generally an example of an active back system.

FIG. 10 illustrates generally an example of an active back system including a stimulation device 110, the stimulation device 110 including a back wrap 161 configured to be worn around a back, stimulating means (e.g., first, second, third, and fourth stimulating means 116A, 116B, 116C, 116D, respectively) configured to provide therapy to the back, and a housing 131 configured to store a microcontroller configured to control at least a portion of at least one of the first, second, third, or fourth stimulating means 116A, 116B, 116C, 116D. In an example, the back wrap 161 can be positioned in place securely about the back using fasteners, such as hook and loop fasteners located at opposite ends of the back wrap 161.

In an example, the active back system can be configured to deliver PEMF therapy (e.g., a pulsed RF signal) to a target tissue using one or more applicator coils (e.g., first and second applicator coils, or any other number of applicator coils), as well as thermal therapy (e.g., heat therapy) using one or more disposable, single-use air activated pods, to a target area of the back. In certain examples, the first through fourth stimulating means 116A, 116B, 116C, 116D, can include at least one of an applicator coil or a thermal pod. In an example, the PEMF or thermal therapies can be provided on one or more sides of the spine, in one or more areas of pain due to various reasons (e.g., surgery, arthritis, poor posture, etc.), such as the lumbar region of the back.

In an example, to reduce cost, but still provide therapy to the subject, a sub-set of stimulating means can include both the applicator coil and the thermal pod, while others include only a thermal pod (e.g., the lower stimulating means including applicator coils and thermal pods, and the upper stimulating means including only thermal pods, etc.). Further, the applicator coils or the thermal pods can be placed in one or more other locations about the back wrap 161 due to the modular design of the system, such as described above.

Active Elbow System

Figure 11:
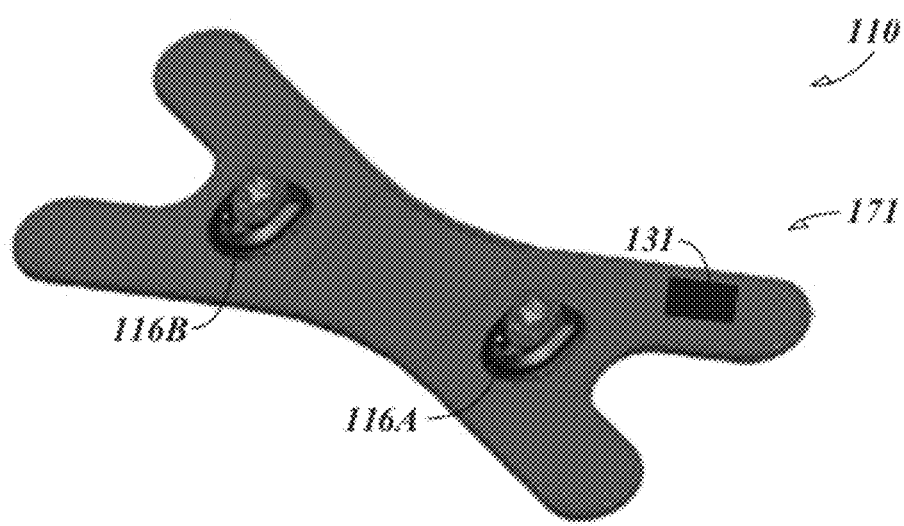
FIG. 11 illustrates generally an example of an active elbow system.

FIG. 11 illustrates generally an example of an active elbow system including a stimulation device 110, the stimulation device 110 including an elbow cuff 171 configured to be worn around an elbow, first and second stimulating means 116A, 116B configured to provide therapy to the elbow, and a housing 131 configured to store a microcontroller configured to control at least a portion of at least one of the first or second stimulating means 116A, 116B. In an example, the elbow cuff 171 can be worn around the elbow, secured in place by fasteners (e.g., hook and loop fasteners located at ends of the elbow cuff 171) in a similar fashion as the active knee system is secured around the knee.

In an example, the first or second stimulating means 116A, 116B can include at least one of an applicator coil or a thermal pod. In an example, the PEMF and thermal therapies can be provided near the medial and lateral sides of the elbow, in certain examples, providing treatment over the lateral epicondyle to treat one or more injuries or condition, such as tennis elbow, etc.

In other examples, the PEMF and thermal therapies can be used to reduce post-surgical pain and edema in the elbow, as well as provide one or more other therapeutic benefits. Using the unique wrap design illustrated in FIG. 11, the elbow cuff 171 can be worn on either the left or right elbow and still provide therapy to the target locations of the elbow without producing different active elbow systems for each side. Further, the applicator coils or the thermal pods can be placed in one or more other locations about the elbow cuff 171 due to the modular design of the system, such as described above.

Active Wrist System

Figure 12:
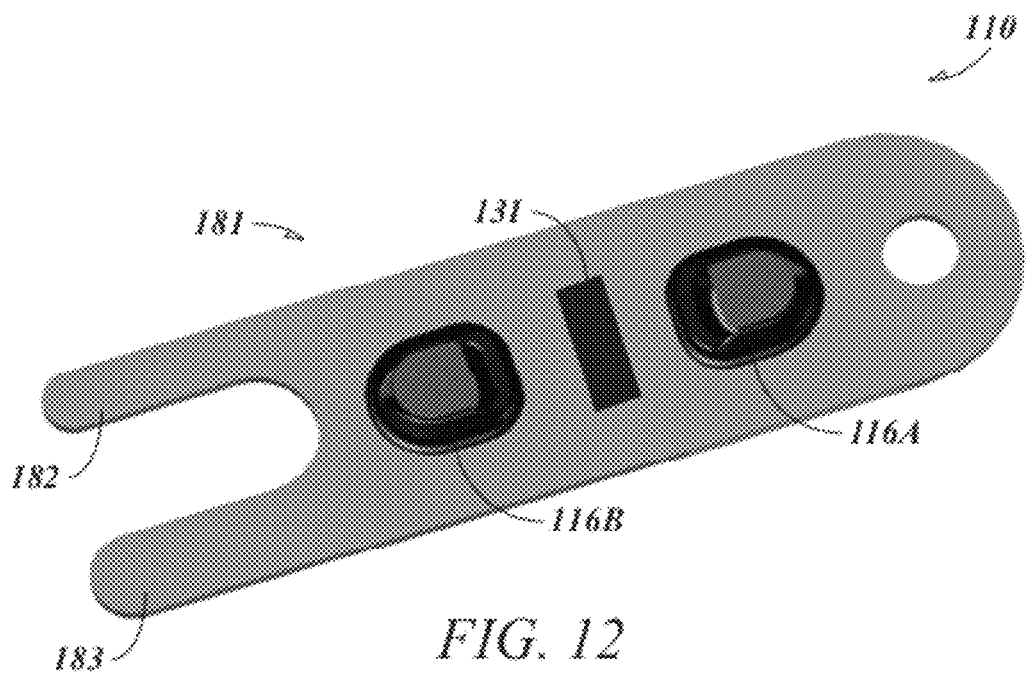
FIGS. 12 and 13 illustrate generally examples of an active wrist system.

FIG. 12 illustrates generally an example of an active wrist system including a stimulation device 110, the stimulation device 110 including a wrist cuff 181 configured to be worn around a wrist, first and second stimulating means 116A, 116B configured to provide therapy to the wrist, and a housing 131 configured to store a microcontroller configured to control at least a portion of at least one of the first or second stimulating means 116A, 116B. In an example, the wrist cuff 181 can be worn by placing the thumb through the hole in the wrist cuff 181 and wrapping the wrist cuff 181 around the wrist. In an example, the wrist cuff 181 can include fasteners, in this example, first and second straps 182, 183. In an example, the fasteners can include hook and loop fasteners, or one or more other type of fastener.

In an example, the first or second stimulating means 116A, 116B can include at least one of an applicator coil or a thermal pod. In an example, the PEMF and thermal therapies can be provided near the medial and lateral areas of the wrist, in certain examples, providing treatment at or near the basal joint, a common location of arthritis. Further, by positioning the applicator coils or the thermal pods at or near the basal joint, treatment over the two collateral ligaments in the wrist is possible.

In other examples, the PEMF or thermal therapies can be used to reduce post-surgical pain and edema in the wrist, as well as provide one or more other therapeutic benefits. Using the unique wrap design illustrated in FIG. 12, the wrist cuff 181 can be worn on either the left or right wrist and still provide therapy to the target locations of the wrist without producing different active wrist systems for each side. Further, the applicator coils or the thermal pods can be placed in one or more other locations about the wrist cuff 181 due to the modular design of the system, such as described above.

Figure 13:
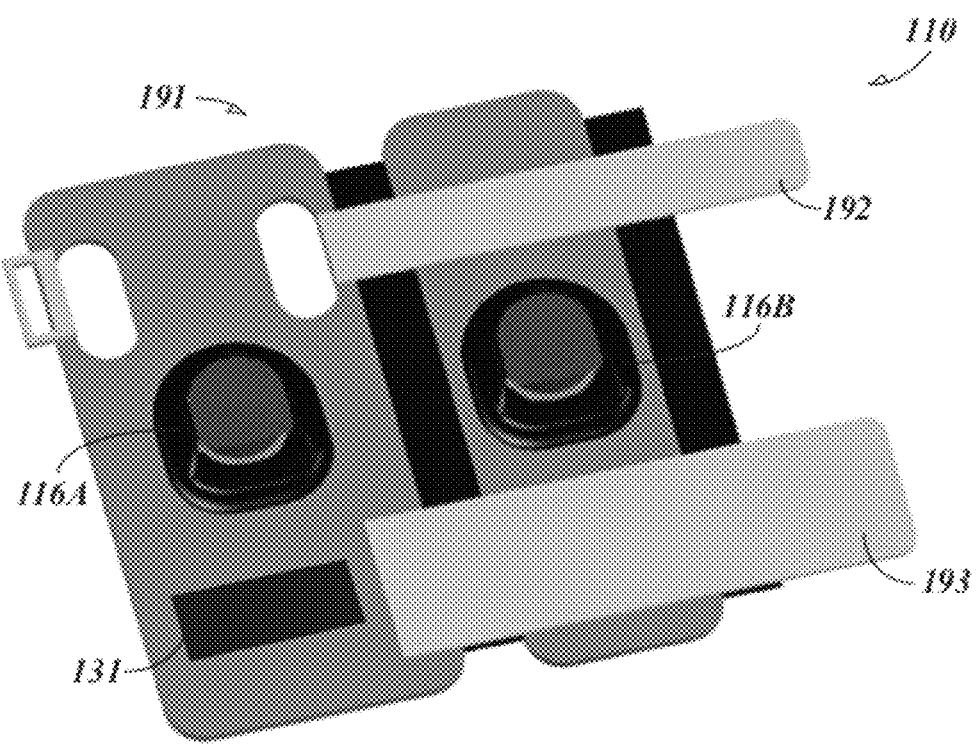

FIG. 13 illustrates generally an example of an active wrist system including a stimulation device 110, the stimulation device 110 including a wrist cuff 191 configured to be worn around a wrist, first and second stimulating means 116A, 116B configured to provide therapy to the wrist, and a housing 131 configured to store a microcontroller configured to control at least a portion of at least one of the first or second stimulating means 116A, 116B. In this example, the thumb can be pushed through the appropriate thumb hole and first and second straps 192, 193 can be adjusted to secure the wrist cuff 191 in place using fasteners, such as hook and loop fasteners, or one or more other fasteners. In an example, the wrist cuff 191 can secure the stimulation first and second stimulating means 116A, 116B over the center of the wrist, allowing the therapy to penetrate deep within the wrist.

In other examples, the PEMF or thermal therapies can be used to reduce post-surgical pain and edema in the wrist, as well as provide one or more other therapeutic benefits. Using the unique wrap design illustrated in FIG. 13, the wrist cuff 191 can be worn on either the left or right wrist and still provide therapy to the target locations of the wrist without producing different active wrist systems for each side. Further, the applicator coils or the thermal pods can be placed in one or more other locations about the wrist cuff 191 due to the modular design of the system, such as described above.

Reactable Substances

Figure 14:
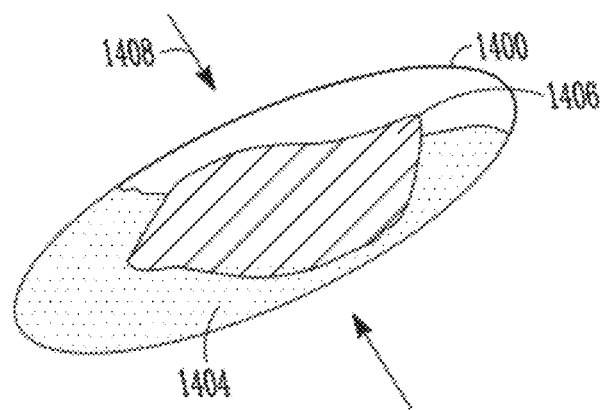
FIG. 14 is a diagram representing two mixable substances, according to an example.

FIG. 14 is a diagram of two reactable substances. A thermal exchange component such as a single-use thermal exchange component can include a thermal exchange source configured to provide heat transfer therapy to a target area such as a joint. The heat transfer therapy can include heating (i.e., exothermic heat transfer) or cooling (i.e., endothermic heat transfer). A heat transfer source can include substances mixable to undergo a reaction. The thermal exchange component can maintain a temperature above or below that of the target area, depending on the therapy prescribed by a caregiver and/or desired by a user.

At least two substances can react upon mixing to produce thermal energy exchangeable with the joint. Examples are included wherein the at least two substances include ammonium nitrate 1404 and water 1406. Some examples include breaking 1408 a breakable barrier, such as a barrier surrounding one of the substances. Water 1406 can be disposed in a pouch that is disposed in a housing 1400 which also includes a salt such as ammonium nitrate. Optionally, ammonium nitrate can be disposed in a pouch that houses a breakable water pouch. A breakable barrier can be a membrane defining two sides of the housing 1400, with reactable substances on each side of the membrane. Accordingly, a user can select the appropriate $EMT^2$, whether for heating or cooling, and pair it with a brace or cuff to provide treatment.

As disclosed herein, a system can include an indicator to display (e.g. 130) to a user whether the therapy provided is heating or cooling. A display of a first indicia, e.g. a first color, shape and/or pattern can indicate heating, and a display of a second indicia, e.g. a second color, shape and/or pattern, can indicate cooling.

Thermal therapy embodiments disclosed herein are not limited to reactable substances, and can include other substances, such as heat storage devices such as heat capacitors that can be charged before use such as by pre-heating before use or pre-cooling before use, powered refrigeration devices, powered heating devices and other heat transfer devices. An example includes a pack placed into refrigeration before use, and a pack heated before use, such as through radiation, convection and/or conduction, including via microwave excitation of substances in the pack. Another example includes an electronic refrigeration device that can be placed into a pouch to cool a target area. Power for such a pouch can be provided via a power cord or batteries, such as portable batteries wearable on a cuff.

Examples Including Wrap-around Configuration

Figure 15A:
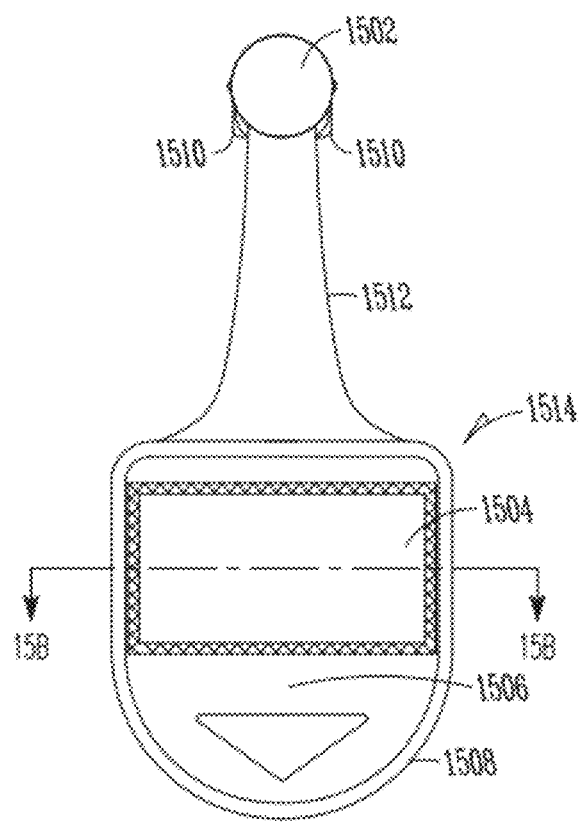
FIG. 15A is a top view of a thermal therapy component assembly including a splay lanyard, according to an example.
Figure 15B:
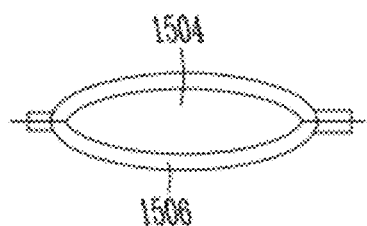
FIG. 15B is a front view of a cross-section of the component of FIG. 15A.

FIGS. 15A-B show views of a thermal therapy component assembly including a component to wrap around a cuff. To wrap around the cuff, examples include a lanyard 1512. As discussed herein by way of examples, on one side of the lanyard 1512 is a housing to couple to a holder to activate electromagnetic therapy and on the other is a thermal therapy component.

In certain examples, the provision of electromagnetic therapy can occur concurrent with the use of a thermal exchange component, such as during the reaction of two substances 1504, 1506 to exchange heat with a target location such as a joint. For example, a brace such as a cuff can include at least some components used to provide electromagnetic field stimulation, and those components can be deactivated until a thermal exchange component is coupled with the brace in a manner to activate the electromagnetic field stimulation.

In certain examples, a housing 1502 is mateable to a holder fixed to a cuff and is also coupled to the thermal exchange component 1514. Mating the housing 1502 to the holder can activate electromagnetic therapy. The electromagnetic field can be activated to provide therapy, such as pulsed electromagnetic therapy, sequential with or concurrent to provision of thermal exchange therapy.

Examples are included wherein the disposable housing 1502 includes a conductor (e.g., 1704 as illustrated in FIG. 17I) to electrically and physically bridge an open circuit (e.g., by making contact with contacts 142A) of the electromagnetic stimulator circuit.

A holder (e.g. 125A as illustrated in FIG. 6) can include a retention mechanism such as a notch (e.g. 135A as illustrated in FIG. 6), wherein the disposable housing is configured to be removably inserted into the holder (e.g. 125A) to engage the notch 135A to mechanically affix the disposable housing to the holder. The housing can include protrusions 1510 to engage the notch 135A. Upon engagement, therapy can be activated.

As referenced herein, therapy can be sequential with or concurrent with heat transfer with a joint, such as by breaking of the breakable barrier to mix two substances and react them.

Examples are included wherein the disposable housing 1502 is coupled to the thermal therapy component 1514 via a lanyard 1512 sized to wrap from an outer portion of a cuff to the inner portion of a cuff.

In the example, an internal pouch 1504 is welded inside an outer pouch 1506 with a common weld that extends on opposite sides of each of the first pouch and the second pouch. A cross section of the concurrent welding and attachment of the inner pouch to the outer pouch is shown in FIG. 15B. Such an approach can simplify manufacturing and reduce cost.

Figure 16A:
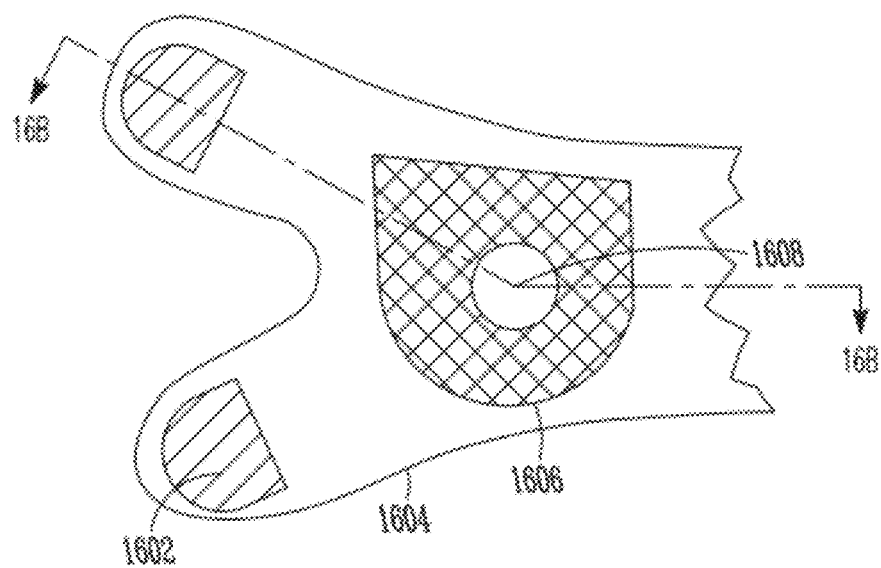
FIG. 16A shows a front view of a portion of an inner portion of a cuff, including a pouch.
Figure 16B:
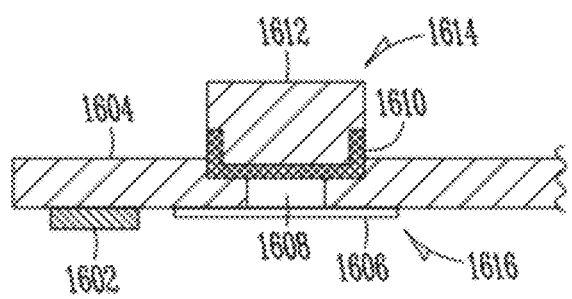
FIG. 16B shows a top view of the cuff of FIG. 16A.

FIGS. 16A-B shows a portion of an inner portion of a cuff 1604, including a pouch 1606. The cuff can be attached the joint in part by fastening fasteners 1602. The fasteners 1602 can include adhesives, hook-and-loop fasteners, one or more snap-fit connectors and other fasteners.

Examples include wrapping a lanyard around the cuff, including connecting a housing 1612 and a thermal therapy component to the cuff with the lanyard extending from an outer side 1614 of the cuff 1604 to an inner side 1616. Some examples include removably coupling a housing 1612 to a holder 1610 on the outer side 1614 of the cuff 1604 to activate the generating of the electromagnetic field. A thermal therapy component can be inserted in a pouch, such as a pouch shaped to conform to the thermal therapy component to hold it snugly in place. The illustrated pouch 1606 has a semi-circular bottom sized to conform to a semicircular bottom of a thermal therapy component. Such conforming shape can provide conform and assist users in orienting the thermal therapy component, which is important considering that a lanyard can wrap around a cuff 1604 to position a housing 1612 proximal a holder 1610 such that the housing 1612 can be inserted in the holder 1610.

The pouch 1606 can comprises netting, as illustrated. Such a configuration can provided from improved thermal conduction from a thermal therapy component, through the pouch 1606, to the target location, e.g. a joint. The present subject matter is not limited to configuration in which the pouch 1606 is formed of netting, and can include other configuration, such as configuration in which the pouch 1606 is formed of another medium compatible with efficient heat transfer.

Examples are included wherein the cuff 1604 defines an aperture 1608 extending through the cuff 1604 and opening to the holder 1610. Some examples include an aperture 1608 opening to a bottom aperture of the holder 1610. An aperture 1608 can allow for a housing 1612 to contain a thermal therapy component to transfer heat from the thermal therapy component to the target site through the aperture 1608. Heat transfer as referenced herein can include one or more of radiation, convection and conduction.

As referenced herein, certain examples are included wherein the disposable housing 1612, when mechanically coupled to the holder 1610, is configured to enable the electromagnetic stimulator circuit to generate the electromagnetic field within the joint. Examples are included wherein the reaction is endothermic and comprising an indicator circuit configured to display a first color while the disposable housing 1612 is inserted in a holder 1610, and a second color while a second disposable housing 1612, including a hot pack, is inserted in the holder 1610.

FIGS. 17A-I show several views of a housing 1702 such as a disposable housing. The housing includes a metal plate or conductor 1704. A window 1706 exposes the conductor to other components, providing for interconnect between the conductor 1704 and the other components. As illustrated, the housing 1702 can include an inner hollow 1708. However, a heat transfer device, either endothermic or exothermic in nature, can be disposed in the hollow 1708. The housing 1702 can include protrusions 1710 that can engage a notch (e.g. 135A as illustrated in FIG. 6).

FIGS. 18A-C are cross sections of the component of FIG. 18B, taken along line 18A-18A, according to an example. The embodiment shows a lanyard having a straight shape instead of a splayed shape as illustrated in FIGS. 15A-B. In the illustration, a housing 1802 is coupled to a thermal therapy component 1808 via the lanyard 1804. A cross section illustrated in FIG. 18A shows a pouch 1808, such as one filled with salt, disposed in another pouch 1806, such as one filled with water. Puncture of the pouch 1808 can begin a reaction, such as an endothermic reaction.

Figure 19:
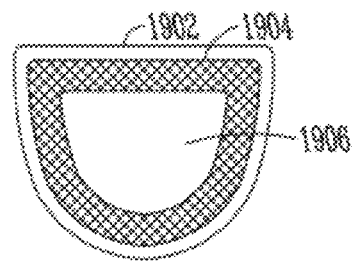
FIG. 19 illustrates a hook-and-loop configuration for attaching a thermal therapy component to a cuff, according to an example.

FIG. 19 illustrates a hook-and-loop configuration for attaching a thermal therapy component to a cuff, according to an example. The example shows a thermal therapy component 1904 including hook-and-loop features 1904 that can be used to affix the thermal therapy component 1902 to a cuff. The hook-and-loop feature can form a perimeter around an open portion 1906. The open portion 1906 can improve heat transfer from the thermal therapy component 1904 to a joint. The open portion 1906 can also couple with a housing to enable the housing to activate electromagnetic stimulation therapy, such as by coupling electrical contacts of the housing to those of a holder to close a circuit. The open portion 1906 can face the joint directly, or could face the joint through an aperture such as the aperture 1608 illustrated in FIGS. 16A-B.

Figure 20B:
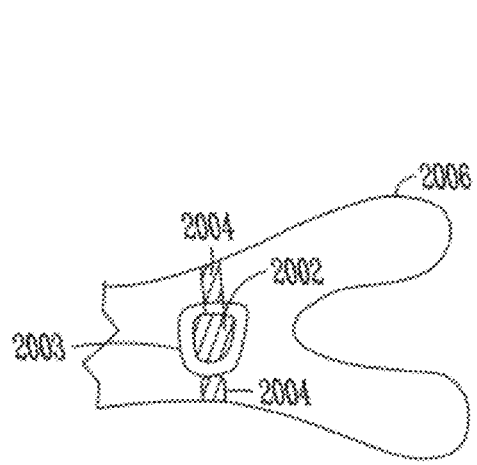
FIG. 20B is a partial view of a cuff with the thermal therapy component of 20A attached, according to an example.
Figure 20A:
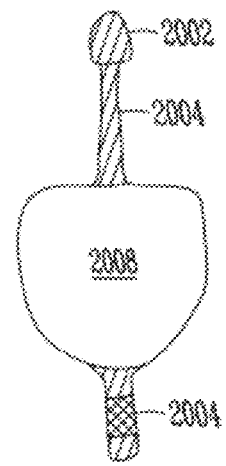
FIG. 20A is a front view of an unsecured thermal therapy component include a hook strap, according to an example.

FIGS. 20A-B show two modes of attachment of a thermal therapy component. A thermal therapy component 2008 can be coupled to an inner portion of a cuff 2006 by attaching an anchor 2004, such as to an outer part of the cuff 2006, positioning the thermal therapy component 2008 in a desired location on the inner portion of the cuff, wrapping a lanyard 2004 around the cuff from the inner portion to the outer portion, and attaching the lanyard to a housing 2002 and/or a holder 2003. In an example, the attachment feature 2002 can comprise a housing or a barb that can be inserted into a housing. Either of a barb insertable in a housing, or a housing, can include a conductor that can complete an open circuit in the holder 2003, such as by bridging contacts exposed inside the holder 2003.

Figure 21:
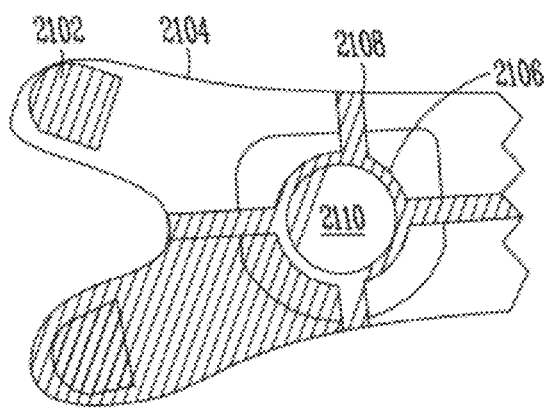
FIG. 21 is a partial view of a cuff with the thermal therapy component attached via multiple straps, according to an example.

FIG. 21 is a partial view of a cuff with the thermal therapy component attached via multiple straps, according to an example. A thermal therapy component 2110 can be coupled to a cuff 2104 by attaching by positioning the thermal therapy component 2110 in a desired location, wrapping multiple lanyards 2108 around the cuff 2104 and attaching the lanyards to the cuff 2104, such as with a fastener 2004, such as a barb. In an example, some portion of the lanyard 2108 can provide a conductor to activate an electromagnetic therapy circuit of the cuff 2104, such as by bridging an open circuit inside a holder, or a housing inserted in a holder. For example, a housing can be coupled with the lanyard 2108 and can be inserted in a holder. The barb in FIG. 22 can be used to connect the thermal therapy component to the housing to close an open circuit in the housing.

Figure 22:
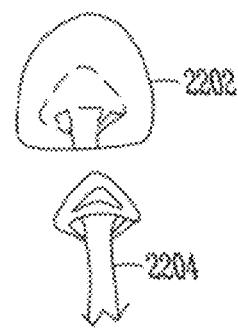
FIG. 22 is a partial view of a male connector and a female connector to attached a thermal therapy component to itself, according to an example.

FIG. 22 is a partial view of a male connector and a female connector to attached a thermal therapy component to itself, according to an example. In an example a barb 2204 can be inserted into a housing 2202 that is insertable in a holder. In an example, a barb 2204 includes a conductor that can be inserted into a housing 2202 to close an open circuit in the housing.

Figure 23:
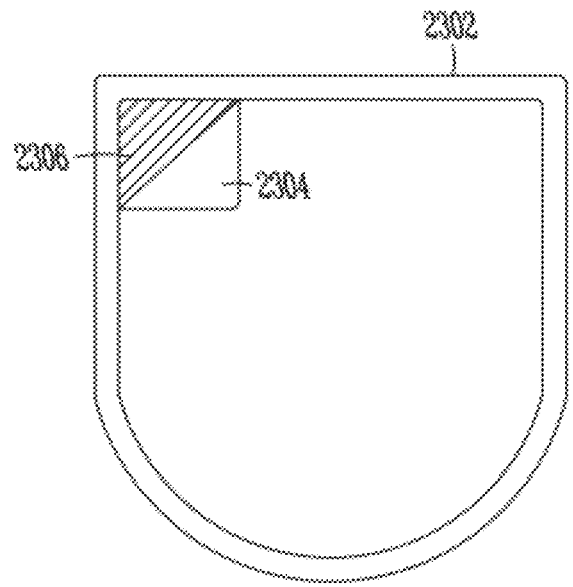
FIG. 23 is a view of an adhesive thermal therapy component, according to an example.

FIG. 23 is a view of an adhesive the thermal therapy component, according to an example. In the example, a thermal therapy component 2302 can be adhered to a cuff such as be removing a release 2304 to expose an adhesive 2306 configured to adhere the thermal therapy assembly to a joint or a cuff. Examples can include hook-and-loop to attach the thermal therapy component 2302 to a cuff. In an example, the cuff is comprised of soft loops, and the thermal therapy component 2302 includes hooks to attach to the soft loops. The converse is possible.

Some examples include one or more mechanical snap-fit type fasteners to attach the cuff. In an example, a number of such fasteners are placed at regular or random positions along a perimeter of the thermal therapy component 2302.

Figure 24:
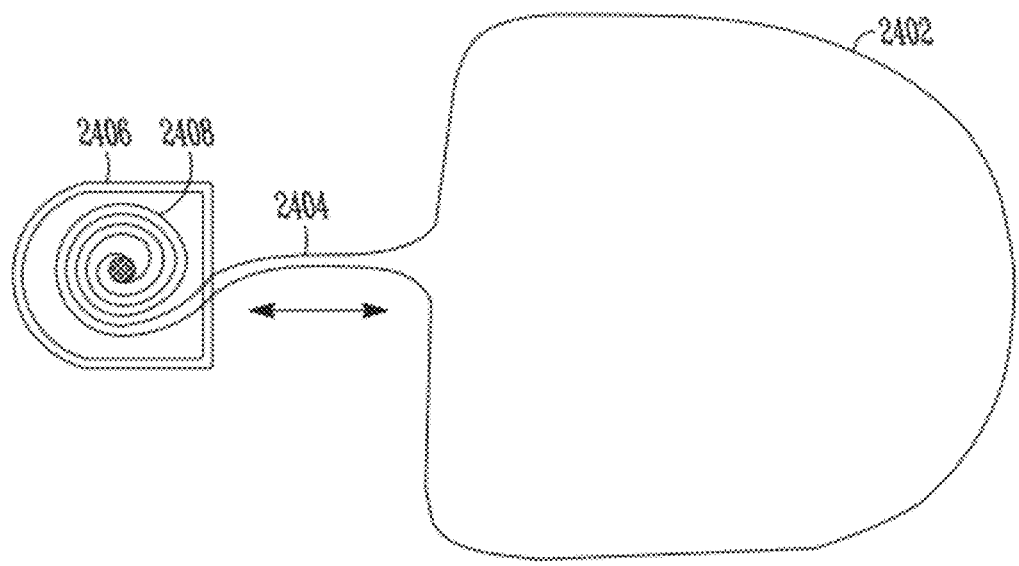
FIG. 24 is a view of a thermal therapy component coupled with a thermal therapy component via a retractable lanyard, according to an example.

FIG. 24 is a view of a thermal therapy component coupled with a thermal therapy component via a retractable lanyard, according to an example. In an example, a thermal therapy component 2402 is coupled with a housing 2406 via a lanyard 2404. In an example, the lanyard 2404 is retractable into one or both of a thermal therapy component 2404 and a housing 2406. In an example, a clock-spring configuration 2408 is used to retract the lanyard into the housing 2406.

FIG. 25A is a partial view of a cuff with the thermal therapy component attached via hook-and-loop, according to an example. FIG. 25B is a cross section of the component of FIG. 25B, taken along line 25B-25B, according to an example. In an example, a holder 2508 can receive a housing 2506 that is attached to a lanyard 2504 that can wrap around a cuff 2502. The housing exterior 2510 can be exposed to heat or cold, and insulation 2512 can insulate the housing such at the housing assembly 2504 insulates the cuff and the holder 2508 against heat transfer.

FIG. 26 is a partial view of a cuff with a heat conductive pouch, according to an example. The example shows a cuff 2604 including fasteners 2602, such as hook-and-loop fasteners, and a pouch 2606, which in the illustrated example is formed of a conductive material such as a foil.

FIG. 27A is a perspective view of a thermal therapy component including a pod and an anchor, according to an example. FIG. 27B is a perspective view of a thermal therapy component assembly deployed, according to an example. In the example, a thermal therapy component 2702 includes a first substance 2718 and a second substance 2716, such as ammonium nitrate. An anchor 2712 can couple the thermal therapy component to a cuff, and a housing 2704 can be pulled away from the anchor. Pulling the housing 2704 away from the anchor tears a pouch including a first portion 2706 and a second portion 2708 along a seam 2710, breaking a barrier between the first substance 2716 and the second substance 2718, enabling a reaction between them. The housing 2704 can then wrap around a cuff and be inserted into a holder to enable commencement of electromagnetic therapy.

Figure 28B:
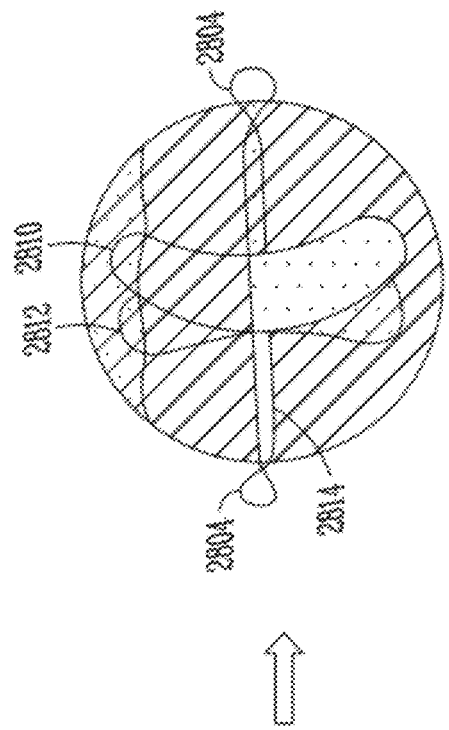
FIG. 28B is a perspective view of a thermal therapy component assembly deployed, according to an example.
Figure 28A:
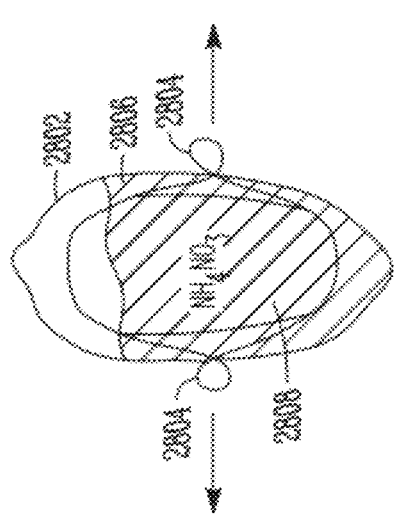
FIG. 28 A is a perspective view of a thermal therapy component including opposing seam handles, according to an example.

FIG. 28A is a perspective view of a thermal therapy component including opposing seam handles, according to an example. FIG. 28B is a perspective view of a thermal therapy component assembly deployed, according to an example. In the example, handles 2804 can be pulled away from one another, which can cause cord 2814 to slice a first portion of a barrier pouch 2810 from a second portion of the barrier potion 2812, releasing a first substance 2808 such as ammonium nitrate into a second substance 2806 such as water, to enable a reaction between them.

Figure 29A:
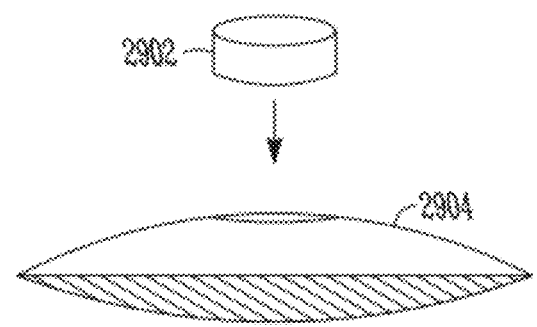
FIG. 29A is a perspective view of a thermal therapy component assembly, according to an example.
Figure 29B:
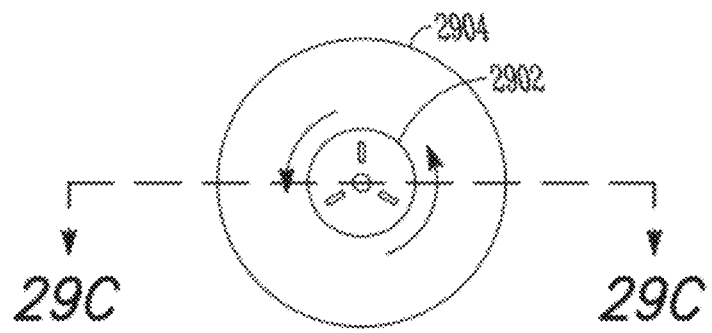
FIG. 29B is a top view of the assembly of FIG. 29A, according to an example.
Figure 29C:
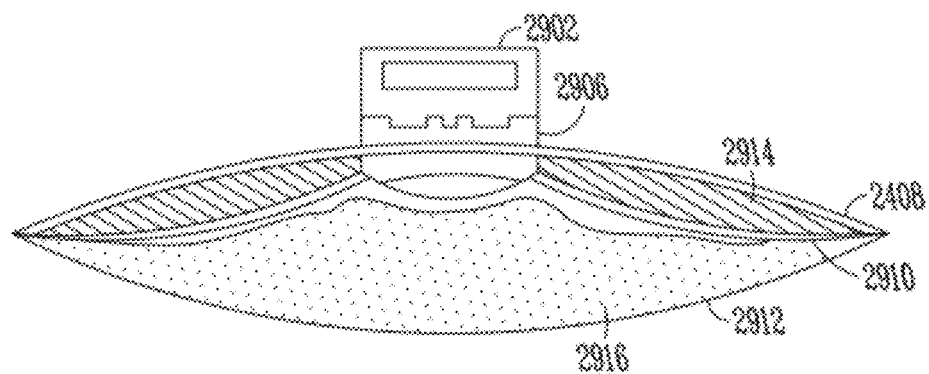
FIG. 29C is a cross-section taken along line 29C-29C in FIG. 29B, according to an example.
Figure 29D:
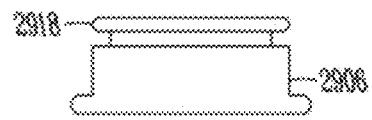
FIG. 29D is a top view of a spool operable with the assembly of FIG. 29A, according to an example.

FIG. 29A is a perspective view of a thermal therapy component assembly, according to an example. FIG. 29B is a top view of the assembly of FIG. 29A, according to an example. FIG. 29C is a cross-section taken along line 29C-29C in FIG. 29B, according to an example. FIG. 29D is a top view of a spool operable with the assembly of FIG. 29A, according to an example.

In the example, pouch 2904 assembly containing two substances can be engaged to mix them, while also bridging an open circuit. In the example, a holder 2906 includes a spool 2906. The spool can include a recess 2918 that can rotably seal to the pouch 2912. The spool can be fixed to a breakable barrier 2910. In an example, a housing 2902 can be inserted in the holder 2906 and can be keyed to an interior of the holder to enable torque transmission from the housing 2902 to the holder/spool 2906. Rotation of the holder can break the barrier 2910, enabling a first substance 2912 to mix with a second substance 2916.

Figure 30A:
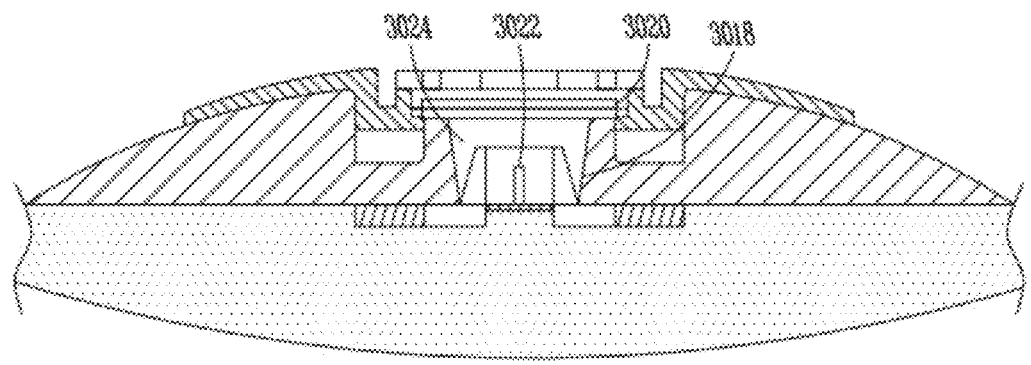
FIG. 30A is a cross-section of a thermal therapy component assembly, according to an example.
Figure 30B:
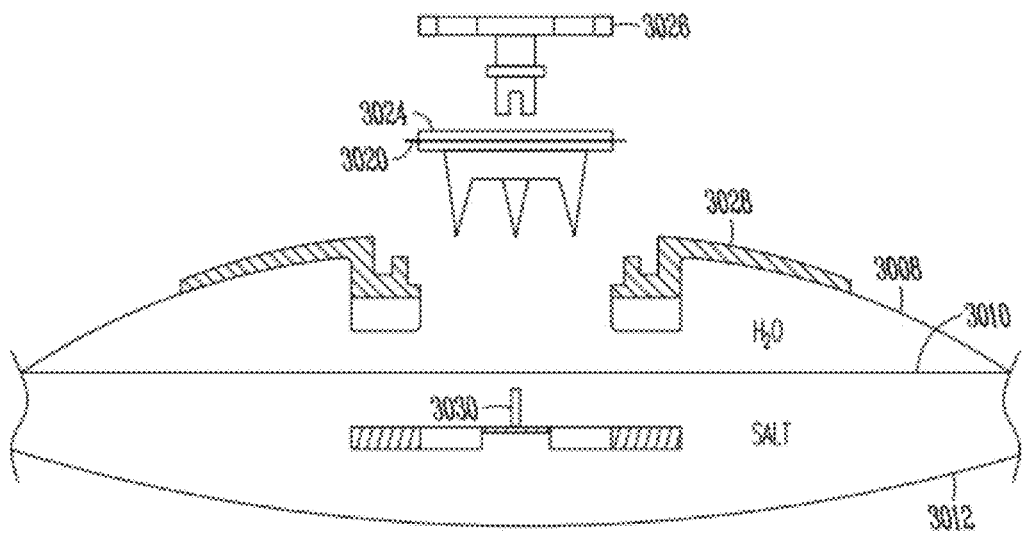
FIG. 30B is an exploded view of the thermal therapy component assembly of FIG. 30A.
Figure 30E:
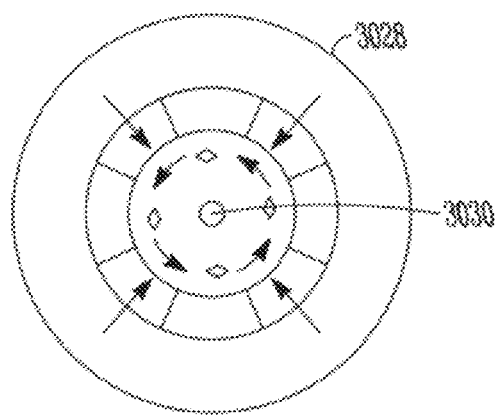
FIG. 30E is a top view of the housing of the thermal therapy component of FIG. 30B, according to an example.

FIG. 30A is a cross-section of a thermal therapy component assembly, according to an example. FIG. 30B is an exploded view of the thermal therapy component assembly of FIG. 30A. FIG. 30C is a perspective view of a spool operable in the assembly of FIG. 30A. FIG. 30I) is a side view of the spool of FIG. 30C, according to an example. FIG. 30E is a top view of the housing of the thermal therapy component of FIG. 30B, according to an example.

In an example, a pouch 2008 can include a breakable barrier 3010 separating a first substance H20 from a second substance salt, although other substances are possible. In the example, a holder 3028 is coupled to the pouch. A bottom portion of the holder 3030 is attachable to a top portion to define openings that extend radially away from a center pin 3022. A cutter 3024 can be inserted in the holder, sealed to the holder with a seal 3020, to rotate around the center pin 3022.

In an example, a key 3026 can be inserted in the cutter 3024 which can force the cutter down into the barrier 3010 to cut the battier. The key 3026 can be rotably sealed by a seal 3027 such as an o-ring. A spring 3032 can bias the cutter away from cutting the barrier 3010. A housing 3034 can be keyed to the key 3026 to enable torque transfer from the housing 3034 to the key 3026. Thus actuating the housing 3034 can force the key down into the cutter 3024, and can rotate the cutter to break the barrier 3010 and allow for flow as shown with radial flow lines in FIG. 30E. The flow can enable mixing of two substances to enable their reaction with one another.

Figure 31:
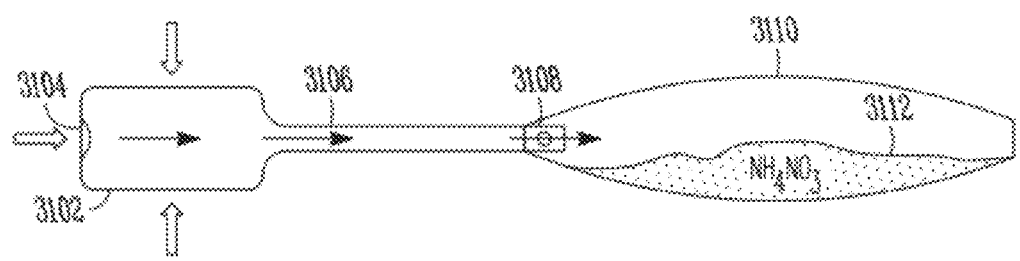
FIG. 31 is a side view of a thermal therapy component assembly including a pump, according to an example.

FIG. 31 is a side view of a thermal therapy component assembly including a pump, according to an example. In an example, a pump 3102 can pump fluid, such as from an inlet 3104, down a lumen 3106 and into a thermal therapy component 3110 to reactive the fluid with another substance 3112 such as ammonium nitrate. An optional check valve 3108 can be used to ensure that the substances react in a sealed environment. The pump 3102 can optionally include a conductor to enable electromagnetic stimulation. Accordingly, the pump 3102 can optionally be inserted into a holder, such as by wrapping the lumen 3106 around a cuff.

Figure 32:
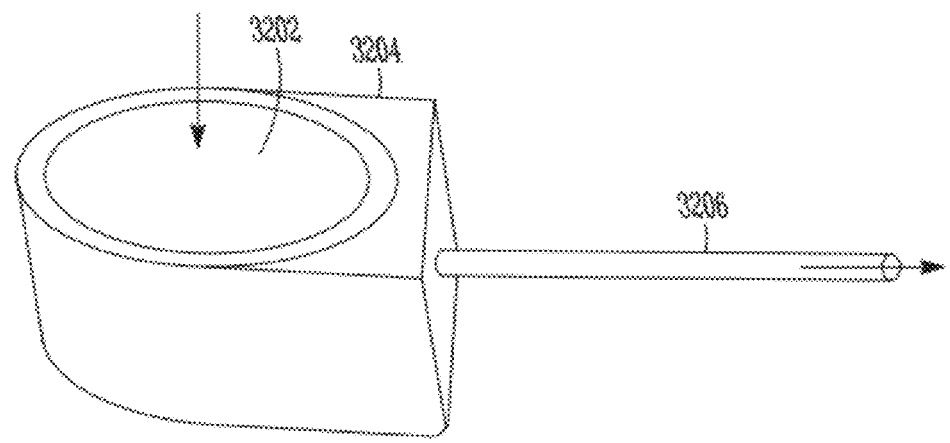
FIG. 32 is a side view of a thermal therapy component assembly attachable to a faucet, according to an example.

FIG. 32 is a side view of a thermal therapy component assembly attachable to a faucet, according to an example. In the example, a fitting 3204 is affixable to a fluid outlet, such as a water faucet, to enable to flow of fluid into an inlet 3202 and down a lumen 3206 toward a thermal therapy component. As with FIG. 31, the thermal therapy component can include a substance reactable with the fluid. A check valve can optionally be used to limit the flow of fluid through the lumen 3106 to one direction.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A portable, non-invasive system for providing therapeutic treatment to a joint to promote healing of the joint, the system comprising:
   a cuff positionable around the joint, the cuff including:
      an electromagnetic stimulator circuit coupled to the cuff and configured to provide an electromagnetic field within the joint; and
      a thermal therapy component coupleable to the cuff, the thermal therapy component comprising:
         an activation circuit that, when coupled to the cuff, is configured to activate the electromagnetic stimulator circuit; and
         at least two substances in separate compartments separated by a breakable barrier, wherein the at least two substances are configured to react upon mixing to produce thermal energy exchangeable with the joint;
      a holder coupled to the cuff proximate the electromagnetic stimulator circuit;
      a pouch coupled to the cuff and sized to receive the thermal therapy component; and
      wherein the thermal therapy component includes a disposable housing configured to be mechanically coupled to the holder,
      wherein the disposable housing includes a conductor to electrically and physically bridge an open circuit of the electromagnetic stimulator circuit when coupled to the holder, and
      wherein the activation circuit includes the conductor.

2. The system of claim 1, wherein the holder is on an outer portion of the cuff and the pouch is on an inner portion of the cuff.

3. The system of claim 2, wherein the disposable housing is coupled to the remainder of the thermal therapy component via a lanyard sized to wrap from the outer portion of the cuff to the inner portion of the cuff.

4. The system of claim 1, wherein the cuff defines an aperture extending through the cuff and opening to the holder, including opening to a bottom aperture of the holder.

5. The system of claim 1, wherein the holder includes a notch, and wherein the disposable housing is configured to be removably inserted into the holder to engage the notch to mechanically affix the disposable housing to the holder.

6. The system of claim 1, wherein the disposable housing, when mechanically coupled to the holder, is configured to enable the electromagnetic stimulator circuit to generate the electromagnetic field within the joint.

7. The system of claim 6, wherein the reaction is endothermic and comprising an indicator circuit configured to display a first color while the disposable housing is inserted in a holder, and a second color while a second disposable housing, including a hot pack, is inserted in the holder.

8. The system of claim 7, wherein said at least two substances include ammonium nitrate and water.

9. The system of claim 7, wherein the second disposable housing includes a medial disposable housing including a single-use exothermic exchange component, the medial disposable housing configured to be mechanically, removably coupled to a medial holder on the cuff, and also comprising a lateral disposable housing including a single-use exothermic exchange component, the lateral disposable housing configured to be mechanically, removably coupled to a lateral holder on the cuff.

10. A portable, non-invasive system for providing therapeutic treatment to a joint to promote healing of the joint, the system comprising:
a cuff positionable around the joint, the cuff including:
an electromagnetic stimulator circuit configured to provide an electromagnetic field within the joint; and
a thermal therapy component coupleable to the cuff, the thermal therapy component comprising at least two substances in separate compartments separated by a breakable barrier, wherein the at least two substances are configured to react upon mixing to produce thermal energy exchangeable with the joint;
a holder coupled to the cuff proximate the electromagnetic stimulator circuit;
a pouch coupled to the cuff and sized to receive the thermal therapy component; and
a disposable housing coupled to the thermal therapy component, the disposable housing configured to be mechanically coupled to the holder,
wherein the disposable housing includes a conductor to electrically and physically bridge an open circuit of the electromagnetic stimulator circuit when the disposable housing is mechanically coupled to the holder.

11. The system of claim 10, wherein the holder is on an outer portion of the cuff and the pouch is on an inner portion of the cuff.

12. The system of claim 11, wherein the disposable housing is coupled to the remainder of the thermal therapy component via a lanyard sized to wrap from the outer portion of the cuff to the inner portion of the cuff.

13. The system of claim 10, wherein the holder includes a notch, and wherein the disposable housing is configured to be removably inserted into the holder to engage the notch to mechanically affix the disposable housing to the holder.

14. The system of claim 10, wherein the disposable housing, when mechanically coupled to the holder, is configured to enable the electromagnetic stimulator circuit to generate the electromagnetic field within the joint.

15. The system of claim 10, wherein the reaction is endothermic and comprising an indicator circuit configured to display a first color while the disposable housing is inserted in a holder, and a second color while a second disposable housing, including a hot pack, is inserted in the holder.

16. The system of claim 15, wherein said at least two substances include ammonium nitrate and water.

17. The system of claim 15, wherein the second disposable housing includes a medial disposable housing including a single-use exothermic exchange component, the medial disposable housing configured to be mechanically, removably coupled to a medial holder on the cuff, and also comprising a lateral disposable housing including a single-use exothermic exchange component, the lateral disposable housing configured to be mechanically, removably coupled to a lateral holder on the cuff.

* * * * *